US008802786B2

(12) United States Patent
Shi et al.

(10) Patent No.: US 8,802,786 B2
(45) Date of Patent: Aug. 12, 2014

(54) PARTICULATE SUPERABSORBENT POLYMER COMPOSITION HAVING IMPROVED PERFORMANCE PROPERTIES

(75) Inventors: Yaru Shi, Greensboro, NC (US); Gonglu Tian, Greensboro, NC (US); Mark Joy, Greensboro, NC (US); Geoff Blake, Kernersville, NC (US); Scott Smith, Dusseldorf (DE); Bernfried Messner, Greensboro, NC (US)

(73) Assignee: Evonik Corporation, Parsippany, NJ (US)

( * ) Notice: Subject to any disclaimer, the term of this patent is extended or adjusted under 35 U.S.C. 154(b) by 782 days.

(21) Appl. No.: 13/091,844

(22) Filed: Apr. 21, 2011

(65) Prior Publication Data
US 2012/0267570 A1 Oct. 25, 2012

(51) Int. Cl.
*C08F 8/00* (2006.01)
*C09K 3/00* (2006.01)
*A61L 15/60* (2006.01)
*B01J 20/26* (2006.01)
*C08F 220/06* (2006.01)
*C08J 3/24* (2006.01)

(52) U.S. Cl.
CPC .............. *C08F 220/06* (2013.01); *A61L 15/60* (2013.01); *B01J 20/267* (2013.01); *B01J 20/261* (2013.01); *C08J 3/245* (2013.01); *B01J 2220/68* (2013.01); *C08J 2333/02* (2013.01)
USPC ....................................... 525/330.2; 252/194

(58) Field of Classification Search
CPC .................................. B01J 20/26; C09K 3/00
USPC ....................................................... 525/330.2
See application file for complete search history.

(56) References Cited

U.S. PATENT DOCUMENTS

| | | |
|---|---|---|
| 5,451,613 A | 9/1995 | Smith et al. |
| 5,462,972 A | 10/1995 | Smith et al. |
| 5,559,263 A | 9/1996 | Smith |
| 5,837,789 A | 11/1998 | Stockhausen et al. |
| 5,994,440 A | 11/1999 | Staples et al. |
| 6,090,875 A | 7/2000 | Staples et al. |
| 6,124,391 A | 9/2000 | Sun et al. |
| 6,514,615 B1 | 2/2003 | Jones et al. |
| 6,565,981 B1 | 5/2003 | Messner et al. |
| 6,620,889 B1 | 9/2003 | Mertens et al. |
| 6,743,391 B2 | 6/2004 | Sun et al. |
| 6,831,142 B2 | 12/2004 | Mertens et al. |
| 6,841,229 B2 | 1/2005 | Sun et al. |
| 6,906,131 B2 | 6/2005 | Ahmed et al. |
| 7,163,966 B2 | 1/2007 | Joy et al. |
| 7,163,969 B2 | 1/2007 | Ahmed et al. |
| 7,169,843 B2 | 1/2007 | Smith et al. |
| 7,173,086 B2 | 2/2007 | Smith et al. |
| 7,179,862 B2 | 2/2007 | Mertens et al. |
| 7,241,820 B2 | 7/2007 | Smith et al. |
| 7,285,599 B2 | 10/2007 | Mertens et al. |
| 7,291,674 B2 | 11/2007 | Kang et al. |
| 7,312,286 B2 | 12/2007 | Lang et al. |
| 7,335,713 B2 | 2/2008 | Lang et al. |
| 7,399,813 B2 | 7/2008 | Lang et al. |
| 7,427,650 B2 | 9/2008 | Smith et al. |
| 7,482,058 B2 | 1/2009 | Ahmed et al. |
| 7,488,541 B2 | 2/2009 | Ahmed et al. |
| 7,572,864 B2 | 8/2009 | Mertens et al. |
| 7,579,402 B2 | 8/2009 | Ahmed et al. |
| 7,615,579 B2 | 11/2009 | Joy et al. |
| 7,777,093 B2 | 8/2010 | Smith et al. |
| 7,795,345 B2 | 9/2010 | Smith et al. |
| 7,812,082 B2 | 10/2010 | McIntosh et al. |
| 7,816,426 B2 | 10/2010 | Ahmed et al. |
| 7,842,386 B2 | 11/2010 | Loeker et al. |
| 7,910,688 B2 | 3/2011 | Tian et al. |
| 2007/0129495 A1 | 6/2007 | Mertens et al. |
| 2008/0009616 A1 | 1/2008 | Frank et al. |
| 2008/0032888 A1* | 2/2008 | Nakamura et al. ............ 502/402 |
| 2008/0234420 A1 | 9/2008 | Smith et al. |
| 2009/0134357 A1 | 5/2009 | Bub et al. |
| 2009/0191408 A1 | 7/2009 | Tian et al. |
| 2010/0075844 A1 | 3/2010 | Loeker et al. |
| 2010/0100066 A1 | 4/2010 | Azad et al. |
| 2010/0130355 A1 | 5/2010 | Tian et al. |
| 2010/0247916 A1 | 9/2010 | Hamilton et al. |

(Continued)

FOREIGN PATENT DOCUMENTS

| | | |
|---|---|---|
| CA | 2460152 | 10/2009 |
| CN | 02819951 | 8/2007 |

(Continued)

OTHER PUBLICATIONS

International Search Report mailed on Jul. 4, 2012 in PCT/EP2012/055472.

(Continued)

*Primary Examiner* — Hui Chin
(74) *Attorney, Agent, or Firm* — Philip P. McCann; John P. Zimmer; Smith Moore Leatherwood LLP

(57) ABSTRACT

The present invention relates to a particulate superabsorbent polymer composition which absorbs water, aqueous liquids, and blood, and a process to make the superabsorbent polymers, wherein a superabsorbent polymer is surface treated with a neutralized multivalent metal salt solution having a pH value similar as that of human skin. The present invention also relates to particulate superabsorbent polymer composition having high Gel Bed Permeability and high Absorbency Under Load.

28 Claims, 4 Drawing Sheets

(56) References Cited

U.S. PATENT DOCUMENTS

| | | |
|---|---|---|
| 2010/0279860 A1 | 11/2010 | Smith et al. |
| 2010/0311578 A1 | 12/2010 | Smith et al. |
| 2011/0009841 A1 | 1/2011 | Ahmed et al. |
| 2011/0015601 A1 | 1/2011 | Loeker et al. |

FOREIGN PATENT DOCUMENTS

| | | |
|---|---|---|
| EP | 1169372 A1 | 1/2002 |
| EP | 1315528 A1 | 6/2003 |
| EP | 1315770 A1 | 6/2003 |
| EP | 1438354 A1 | 7/2004 |
| WO | 0053664 A1 | 9/2000 |
| WO | 0220068 A1 | 3/2002 |
| WO | 0222717 A1 | 3/2002 |
| WO | 03025054 A1 | 3/2003 |
| WO | 2005108472 A1 | 11/2005 |
| WO | 2010108875 A1 | 9/2010 |

OTHER PUBLICATIONS

Tian et al., U.S. Appl. No. 12/775,984, filed May 7, 2010.
Tian et al., U.S. Appl. No. 13/020,898, filed on Feb. 4, 2011.

* cited by examiner

PARTICULATE SUPERABSORBENT POLYMER COMPOSITION HAVING IMPROVED PERFORMANCE PROPERTIES

FIELD OF THE INVENTION

The present invention relates to particulate superabsorbent polymer compositions which absorb water, aqueous liquids, and blood, and a method to make the superabsorbent polymer compositions. In particular, the present invention relates to superabsorbent polymer compositions having high permeability, which are produced by contacting a superabsorbent polymer with a neutralized multivalent metal salt solution having a pH value close to that of human skin. The present invention also relates to particulate superabsorbent polymer compositions having high gel bed permeability and high absorbency under load.

BACKGROUND OF THE INVENTION

A superabsorbent polymer, or material, in general refers to a water-swellable, water-insoluble polymer, or material, capable of absorbing at least about 10 times its weight, and up to about 30 times or more its weight in an aqueous solution containing 0.9 weight percent sodium chloride solution in water. Examples of superabsorbent polymer may include a crosslinked partially neutralized polymer, including crosslinked polyacrylic acids or crosslinked starch-acrylic acid graft polymers, that are capable of absorbing large amounts of aqueous liquids and body fluids, such as urine or blood, with swelling and the formation of superabsorbent hydrogel, and of retaining the aqueous liquids under a certain pressure in accordance with the general definition of superabsorbent polymer.

The superabsorbent polymer hydrogel may be formed into particles, generally referred to as particulate superabsorbent polymer, wherein the particulate superabsorbent polymer may be post-treated with surface crosslinking, surface treatment, and other surface treatment to form particulate superabsorbent polymer compositions. The acronym SAP may be used in place of superabsorbent polymer, superabsorbent polymer composition, particulate superabsorbent polymer compositions, or variations thereof. A primary use of superabsorbent polymer and superabsorbent polymer compositions is in sanitary articles, such as babies' diapers, incontinence products, or sanitary towels. A comprehensive survey of superabsorbent polymers, and their use and manufacture, is given in F. L. Buchholz and A. T. Graham (editors) in "Modern Superabsorbent Polymer Technology," Wiley-VCR, New York, 1998.

Sanitary articles, such as diapers, generally include an absorbent core that includes about 30-50% of cellulose fiber and about 50-70% of particulate superabsorbent polymer composition. It is a goal of future sanitary articles to make them smaller and thinner, for fit, comfort and aesthetic reasons and from environmental aspects. One way to accomplish this goal is to reduce the amount of fiber material and increase the amount of particulate superabsorbent polymer composition, wherein there may be less than about 30%, or less than about 20%, or less than about 10% of fiber material in the absorbent core. The particulate superabsorbent polymer composition of these next generation diaper constructions must have a sufficiently high stability and permeability in the swollen state, so that liquid can be transported through the swollen gel. In addition, the components of the sanitary articles must be compatible for the user wherein the components must have properties such as pH compatible with baby's skin, which has a pH of about 7.

Superabsorbent polymers may be prepared by initially neutralizing unsaturated carboxylic acids or derivatives thereof, such as acrylic acid, alkali metal (e.g., sodium and/or potassium) or ammonium salts of acrylic acid, alkyl acrylates, and the like in the presence of a caustic treatment, such as sodium hydroxide, and then polymerizing the product with a relatively small amounts of an internal, or monomer, crosslinker such as a di- or poly-functional monomers. The di- or poly-functional monomer materials may serve as covalent internal crosslinking agents to lightly crosslink the polymer chains, thereby rendering them water-insoluble, yet water-swellable. These lightly crosslinked superabsorbent polymers contain a multiplicity of carboxyl groups attached to the polymer backbone. These carboxyl groups generate an osmotic driving force for the absorption of body fluids by the crosslinked polymer network. The particulate superabsorbent polymer may be surface treated with surface crosslinking and surface treatment to enhance the properties of the particulate superabsorbent polymer.

Superabsorbent polymers and particulate superabsorbent polymer compositions, useful as absorbents in absorbent articles such as disposable diapers, need to have adequately high sorption capacity, as well as adequately high gel strength. Sorption capacity needs to be sufficiently high to enable the absorbent polymer to absorb significant amounts of the aqueous body fluids encountered during use of the absorbent article. Gel strength relates to the tendency of the swollen polymer particles to resist deformation under an applied stress, and needs to be such that the particles do not deform under pressure, and fill the capillary void spaces in the absorbent member, or article, to an unacceptable degree, which is generally called "gel blocking", thereby inhibiting the rate of fluid uptake, or the fluid distribution, by the member or article. Once gel-blocking occurs, it can substantially impede the distribution of fluids to relatively dry zones or regions in the absorbent article, and leakage from the absorbent article can take place well before the particles of absorbent polymer in the absorbent article are fully saturated, or before the fluid can diffuse or wick past the "blocking"

Permeability is a measure of the effective connectedness of a porous structure, be it a mat of fiber of a slab of foam or, in the case of this application, particulate superabsorbent polymer and particulate superabsorbent polymer composition, generally referred to as particulate superabsorbent polymer compositions herein, or SAP, and may be specified in terms of the void fraction and extent of connectedness of the particulate superabsorbent polymer compositions. Gel permeability is a property of the mass of particulate superabsorbent polymer compositions as a whole and is related to particle size distribution, particle shape, the connectedness of the open pores, shear modulus and surface modification of the swollen gel. In practical terms, the permeability of the particulate superabsorbent polymer composition is a measure of how rapidly liquid flows through the mass of swollen particles. Low permeability indicates that liquid cannot flow readily through the particulate superabsorbent polymer compositions, which is generally referred to gel blocking, and that any forced flow of liquid (such as a second application of urine during use of the diaper) must take an alternate path (e.g., diaper leakage).

Surface treatment of particulate superabsorbent polymers is already well-known. To improve the permeability of particulate superabsorbent polymers, ionic complexing of the carboxyl groups near the surface using polyvalent metal cations has been disclosed in prior arts. U.S. Pat. No. 6,620,889 discloses superabsorbents which are surface crosslinked with a combination of a polyol and a cation salt in aqueous solution. The salt's anion may be chloride, bromide, sulphate, carbonate, nitrate, phosphate, acetate or lactate. The use of aluminium sulfate as surface treatment for particulate superabsorbent polymer compositions is disclosed in reference WO 2005/108 472 A1, which discloses a process that includes treating a base polymer with a water-soluble multivalent metal salt and an organic acid or its salt. The multivalent metal salt is preferably aluminium sulfate. The organic acid or salt is selected from a range of acids that includes citric acid, glyoxylic acid, glutaric acid, succinic acid, tartaric acid and lactic acid, or alkali or ammonium salts thereof.

However, it is also known that aluminum sulfate is acidic, with a pH value of less than 4, and is well below the pH values of about 7 of human skin. Aluminum sulfate applied on the surface of particulate superabsorbent polymer will generate an acidic surface. Since a sanitary article comprising superabsorbent polymers is in contact with or is otherwise near or next to a user's skin, it is desirable to control the surface pH of superabsorbent polymers in order to reduce the risk of skin irritation.

It is also known that the solubility of aluminum ions and salts thereof such as aluminum sulfate, in water is pH dependent. At pH levels between 4 and 9.5, aluminum sulfate becomes insoluble in water and precipitation occurs, resulting in slurry of aluminum hydroxide. It is known that a slurry is more difficult to handle, than a solution, in a production process.

U.S. Pat. No. 5,559,263 discloses a method for the preparation of an aqueous aluminum solution having a pH between about 5.0 and about 9.0 at a concentration of at least about 3.1 percent by weight of aluminum. The solution comprises citrates as chelating ligands for aluminum ions. The chelating ligands may compete with the carboxyl groups near the surface of particulate superabsorbent polymer to form ionic complexes with aluminium ions, which may diminish the permeability enhancing effects of aluminium ions.

It is therefore an object of the present invention to provide a particulate superabsorbent polymer composition having improved compatibility with human skin. It is also an object of the present invention to provide a particulate superabsorbent polymer composition that exhibits excellent properties such as the ability to maintain high liquid permeability and liquid retention even when the amount of the particulate superabsorbent polymer composition is increased in percent by weight based on the absorbent structure.

SUMMARY OF THE INVENTION

The present invention comprises a process for the production of a particulate superabsorbent polymer composition comprising the following steps: a) providing a particulate superabsorbent polymer; b) preparing a neutralized multivalent metal salt in the form of an aqueous solution having a pH value from about 5 to about 9; and c) applying the neutralized multivalent metal salt solution of step b) on the surface of the particulate superabsorbent polymer, wherein the particulate superabsorbent polymer composition has a degree of neutralization of more than about 25 mol %; and has a Gel Bed Permeability numeric value of at least about $[8000\ e^{-0.18x}]$ Darcy where x is the numeric value of Centrifuge Retention Capacity; a Centrifuge Retention Capacity greater than about 25 g/g and an absorbency under load at 0.9 psi from about 16 g/g to 24 g/g. It has been found that the surface treatment of particulate superabsorbent polymer with a neutralized multivalent metal salt solution increases certain properties of the particulate superabsorbent polymer composition, in particular, gel bed permeability.

An embodiment of the present invention further includes a particulate superabsorbent polymer composition made by the foregoing process. In one embodiment of the present invention, the particulate superabsorbent polymer composition comprising a polymer comprising: a) from about 55 to about 99.9 wt % of polymerizable unsaturated acid group containing monomers; b) from 0 to about 40 wt % of polymerized, ethylenically unsaturated monomers copolymerizable with a); c) from about 0.001 to about 5.0 wt % based on the weight of a) of an internal crosslinking agent; d) from about 0.001 to about 5.0 wt % based on dry particulate superabsorbent polymer composition weight of surface crosslinking agent applied to the particle surface of the superabsorbent polymer; and e) from 0.01 to about 5 wt % based on dry particulate superabsorbent polymer composition weight of a neutralized multivalent metal salt applied to the particle surface, in the form of an aqueous solution having a pH value from about 5 to about 9 wherein the composition has a degree of neutralization of the polymerizable unsaturated acid group containing monomers is more than about 25%; and the particulate superabsorbent polymer composition having the characteristics of a gel bed permeability numeric value GBP at least about $[8000\ e^{-0.18x}]$ Darcy where x is the numeric value of centrifuge retention capacity; a centrifuge retention capacity greater than about 25 g/g, and an absorbency under load at 0.9 psi from about 18 g/g to about 22 g/g.

An embodiment of the present invention further includes a particulate superabsorbent polymer composition particulate superabsorbent polymer composition comprising a polymer comprising: a) from about 55 to about 99.9 wt % of polymerizable unsaturated acid group containing monomers; b) from 0 to about 40 wt % of polymerized, ethylenically unsaturated monomers copolymerizable with a); c) from about 0.001 to about 5.0 wt % based on the weight of a) of an internal crosslinking agent, wherein the components a), b) and c) are polymerized into a hydrogel which is granulated into particulate superabsorbent polymer having a surface; d) from about 0.001 to about 5.0 wt % based on dry particulate superabsorbent polymer composition weight of surface crosslinking agent applied to the surface of the particulate superabsorbent polymer; and e) from 0.01 wt % to about 5 wt % based on dry particulate superabsorbent polymer composition weight of aluminum salt applied to the surface of the particulate superabsorbent polymer, in the form of an aqueous solution having a pH value from about 5 to about 9.0, wherein said aluminum salt solution comprises aluminum cations and anions of a deprotonated hydroxyl mono-carboxylic acid with a molar ratio of carboxylic anions to aluminum cations between about 0.75:1 to about 1.5:1.

In addition, the present invention is directed to absorbent compositions or sanitary articles such as diapers that may contain superabsorbent polymer compositions of the present invention.

Numerous other features and advantages of the present invention will appear from the following description.

BRIEF DESCRIPTION OF THE DRAWINGS

The foregoing and other features, aspects, and advantages of the present invention will become better understood with regard to the following description, appended claims, and accompanying drawings where:

DEFINITIONS

Figure 1:
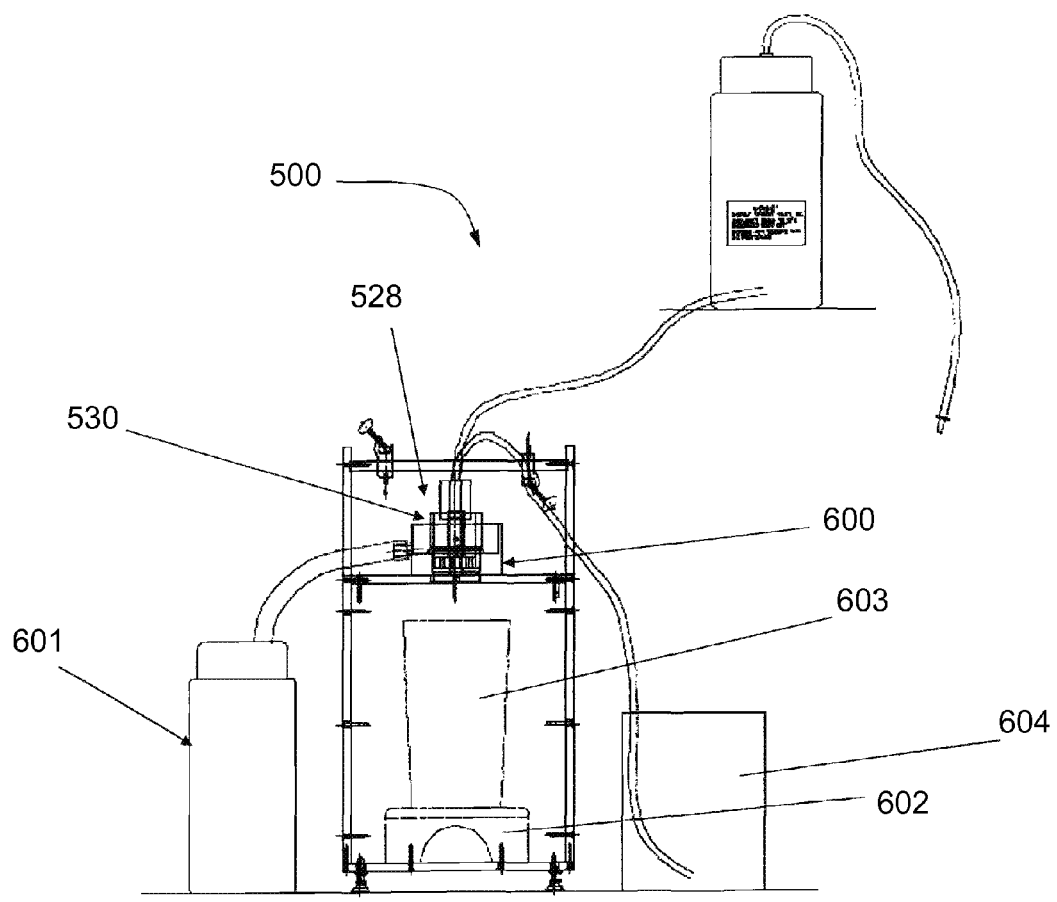
FIG. 1 is a side view of the test apparatus employed for the Free Swell Gel Bed Permeability Test.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities.

The term "absorbent article" as used herein refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. Absorbent articles may further include floor cleaning articles, food industry articles, and the like. As used herein, the term "body fluids" or "body exudates" includes, but is not limited to, urine, blood, vaginal discharges, breast milk, sweat and fecal matter.

The term "Centrifuge Retention Capacity (CRC)" as used herein refers to the ability of the particulate superabsorbent polymer to retain liquid therein after being saturated and subjected to centrifugation under controlled conditions and is stated as grams of liquid retained per gram weight of the sample (g/g) as measured by the Centrifuge Retention Capacity Test set forth herein.

The terms "crosslinked", "crosslink", "crosslinker", or "crosslinking" as used herein refers to any means for effectively rendering normally water-soluble materials substantially water-insoluble but swellable. Such a crosslinking means can include, for example, physical entanglement, crystalline domains, covalent bonds, ionic complexes and associations, hydrophilic associations such as hydrogen bonding, hydrophobic associations, or Van der Waals forces.

The term "internal crosslinker" or "monomer crosslinker" as used herein refers to use of a crosslinker in the monomer solution to form the polymer.

The term "Darcy" is a CGS unit of permeability. One Darcy is the permeability of a solid through which one cubic centimeter of fluid, having a viscosity of one centipoise, will flow in one second through a section one centimeter thick and one square centimeter in cross-section, if the pressure difference between the two sides of the solid is one atmosphere. It turns out that permeability has the same units as area; since there is no SI unit of permeability, square meters are used. One Darcy is equal to about $0.98692 \times 10^{-12}$ m$^2$ or about $0.98692 \times 10^{-8}$ cm$^2$.

The term "diaper" as used herein refers to an absorbent article generally worn by infants and incontinent persons about the lower torso so as to encircle the waist and legs of the wearer and that is specifically adapted to receive and contain urinary and fecal waste.

The term "disposable" as used herein refers to absorbent articles that are not intended to be laundered or otherwise restored or reused as an absorbent article after a single use. Examples of such disposable absorbent articles include, but are not limited to, personal care absorbent articles, health/medical absorbent articles, and household/industrial absorbent articles.

The term "dry particulate superabsorbent polymer composition" as used herein generally refers to the superabsorbent polymer composition having less than about 10% moisture.

The term "gel permeability" is a property of the mass of particles as a whole and is related to particle size distribution, particle shape, and the connectedness of the open pores between the particles, shear modulus, and surface modification of the swollen gel. In practical terms, the gel permeability of the superabsorbent polymer composition is a measure of how rapidly liquid flows through the mass of swollen particles. Low gel permeability indicates that liquid cannot flow readily through the superabsorbent polymer composition, which is generally referred to as gel blocking, and that any forced flow of liquid (such as a second application of urine during use of the diaper) must take an alternate path (e.g., diaper leakage).

The term "mass median particle size" of a given sample of particles of superabsorbent polymer composition is defined as the particle size, which divides the sample in half on a mass basis, i.e., half of the sample by weight has a particle size greater than the mass median particle size, and half of the sample by mass has a particle size less than the mass median particle size. Thus, for example, the mass median particle size of a sample of superabsorbent polymer composition particles is 2 microns if one-half of the sample by weight is measured as more than 2 microns.

The terms "particle," "particulate," and the like, when used with the term "superabsorbent polymer," refer to the form of discrete units. The units can comprise flakes, fibers, agglomerates, granules, powders, spheres, pulverized materials, or the like, as well as combinations thereof. The particles can have any desired shape: for example, cubic, rod like polyhedral, spherical or semi-spherical, rounded or semi-rounded, angular, irregular, et cetera. Shapes having a high aspect ratio, like needles, flakes, and fibers, are also contemplated for inclusion herein. The terms "particle" or "particulate" may also include an agglomeration comprising more than one individual particle, particulate, or the like. Additionally, a particle, particulate, or any desired agglomeration thereof may be composed of more than one type of material.

The terms "particulate superabsorbent polymer" and "particulate superabsorbent polymer composition" refer to the form of superabsorbent polymer and superabsorbent polymer compositions in discrete form, wherein the "particulate superabsorbent polymer" and "particulate superabsorbent polymer compositions" may have a particle size of less than 1000 μm, or from about 150 μm to about 850 μm.

The term "permeability", when used herein shall mean a measure of the effective connectedness of a porous structure, in this case, crosslinked polymers, and may be specified in terms of the void fraction, and extent of connectedness of the particulate superabsorbent polymer composition.

The term "polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to isotactic, syndiotactic, and atactic symmetries.

The term "polyolefin" as used herein generally includes, but is not limited to, materials such as polyethylene, polypropylene, polyisobutylene, polystyrene, ethylene vinyl acetate copolymer, and the like, the homopolymers, copolymers, terpolymers, etc., thereof, and blends and modifications thereof. The term "polyolefin" shall include all possible structures thereof, which include, but are not limited to, isotatic, synodiotactic, and random symmetries. Copolymers include atactic and block copolymers.

The term "superabsorbent polymer" as used herein refers to water-swellable, water-insoluble organic or inorganic materials including superabsorbent polymers and superabsorbent polymer compositions capable, under the most favorable conditions, of absorbing at least about 10 times their weight, or at least about 15 times their weight, or at least about 25 times their weight in an aqueous solution containing 0.9 weight percent sodium chloride.

The term "superabsorbent polymer composition" as used herein refers to a superabsorbent polymer comprising a surface additive in accordance with the present invention.

The term "superabsorbent polymer preproduct" as used herein refers to a material that is produced by conducting all of the steps for making a superabsorbent polymer as described herein, up to and including drying the material, and coarse grinding in a crusher.

The term "surface crosslinking" as used herein refers to the level of functional crosslinks in the vicinity of the surface of the superabsorbent polymer particle, which is generally higher than the level of functional crosslinks in the interior of the superabsorbent polymer particle. As used herein, "surface" describes the outer-facing boundaries of the particle.

The term "thermoplastic" as used herein describes a material that softens when exposed to heat and which substantially returns to a non-softened condition when cooled to room temperature.

The term "% by weight" or "% wt" as used herein and referring to components of the dry particulate superabsorbent polymer composition, is to be interpreted as based on the weight of the dry superabsorbent polymer composition, unless otherwise specified herein.

These terms may be defined with additional language in the remaining portions of the specification.

DETAILED DESCRIPTION OF THE INVENTION

While typical aspects of embodiment and/or embodiments have been set forth for the purpose of illustration, this Detailed Description and the accompanying drawings should not be deemed to be a limitation on the scope of the invention. Accordingly, various modifications, adaptations, and alternatives may occur to one skilled in the art without departing from the spirit and scope of the present invention. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

In one embodiment of the present invention, the superabsorbent polymer composition is a crosslinked polymer comprising: a) from about 55 wt % to about 99.9 wt % of polymerizable unsaturated acid group containing monomers; b) from 0 to about 40 wt % of polymerized, ethylenically unsaturated monomers copolymerizable with a); c) from about 0.001 wt % to about 5.0 wt % based on the weight of a) of internal crosslinking agent; d) from about 0.001 wt % to about 5.0 wt % based on the dry particulate superabsorbent polymer composition weight of a surface crosslinking agent applied to the particle surface; and e) from about 0.01 wt % to about 5 wt % based on the dry particulate superabsorbent polymer composition weight of a neutralized multivalent metal salt solution applied to the particle surface, wherein the composition has a degree of neutralization of more than about 25 mol %.

The aqueous solution of the neutralized multivalent salt may comprise a multivalent cation and an anion of a deprotonated organic acid. The multivalent salt having a pH value same as or close to that of human skin will reduce the risk of skin irritation. In addition, a superabsorbent polymer composition with significantly improved permeability and high absorbency under load is unexpectedly obtained by coating the superabsorbent polymer with the multivalent salt solution having adjusted pH and appropriate molar ratio of organic acid to multivalent cation.

A suitable superabsorbent polymer may be selected from natural, biodegradable, synthetic and modified natural polymers and materials. The term crosslinked used in reference to the superabsorbent polymer refers to any means for effectively rendering normally water-soluble materials substantially water-insoluble but swellable. Such a crosslinking means can include for example, physical entanglement, crystalline domains, covalent bonds, ionic complexes and associations, hydrophilic associations such as hydrogen bonding, hydrophobic associations or Van der Waals forces. Superabsorbent polymers include internal crosslinking and may further include surface crosslinking.

A superabsorbent polymer as set forth in embodiments of the present invention is obtained by the initial polymerization of from about 55% to about 99.9 wt % of the superabsorbent polymer of polymerizable unsaturated acid group containing monomer. A suitable monomer includes any of those containing carboxyl groups, such as acrylic acid, methacrylic acid, or 2-acrylamido-2-methylpropanesulfonic acid, or mixtures thereof. It is desirable for at least about 50 wt %, and more desirable for at least about 75 wt % of the acid groups to be carboxyl groups.

The process to make a superabsorbent polymer as set forth in embodiments of the present invention is obtained by the initial polymerization of from about 55% to about 99.9 wt % of the superabsorbent polymer of polymerizable unsaturated acid group containing monomer. A suitable polymerizable monomer includes any of those containing carboxyl groups, such as acrylic acid, methacrylic acid, or 2-acrylamido-2-methylpropanesulfonic acid, or mixtures thereof. It is desirable for at least about 50% by weight, and more desirable for at least about 75 wt % of the acid groups to be carboxyl groups.

The acid groups are neutralized to the extent of at least about 25 mol %, that is, the acid groups are desirably present as sodium, potassium, or ammonium salts. In some aspects, the degree of neutralization may be at least about 50 mol %. In some aspects, it is desirable to utilize polymers obtained by polymerization of acrylic acid or methacrylic acid, the carboxyl groups of which are neutralized to the extent of from about 50 mol % to about 80 mol %, in the presence of internal cross linking agents.

As to acrylic acid, it is important to use acrylic acid that is known by its contents to be pure, that is the acrylic acid having at least 99.5 wt % concentration, or at least 99.7 wt % concentration, or at least 99.8 wt % concentration. The principal component of this monomer may be either acrylic acid, or acrylic acid and an acrylate salt. Impurities in acrylic acid may include water, propionic acid, acetic acid, and diacrylic acid, commonly called acrylic acid dimer. Content of the diacrylic acid should be 1000 ppm or less, or 500 ppm or less, or 300 ppm or less, when the acrylic acid is used in the process. In addition, it is important to minimize the generation of β-hydroxyproprionic acid during the neutralization process to less than about 1000 ppm, or less than about 500 ppm, of β-hydroxyproprionic acid.

Moreover, in the acrylic acid, the content of protoanemonin and/or furfural is 0 to 20 ppm by weight in terms of the converted value based on acrylic acid. In light of improvement physical properties and characteristics of the water absorbing resin, content of protoanemonin and/or furfural in the monomer is not higher than 10 ppm by weight, or from 0.01 to 5 ppm by weight, or from 0.05 to 2 ppm by weight, or from 0.1 to 1 ppm by weight in terms of the converted value based on acrylic acid.

Further, in the monomer, it is preferred that the amount of aldehyde component other than furfural and/or maleic acid is as small as possible for the same reason. Specifically, the content of the aldehyde component other than furfural and/or maleic acid may be from 0 to 5 ppm by weight, or from 0 to 3 ppm by weight, or from 0 to 1 ppm by weight, or 0 ppm by weight (not higher than detection limit) in terms of the converted value based on acrylic acid. Examples of the aldehyde component other than furfural include benzaldehyde, acrolein, acetaldehyde and the like.

Additionally, in the monomer or particulate water absorbing agent of the present invention, content of saturated carboxylic acid consisting of acetic acid and/or propionic acid, not higher than 1000 ppm by weight, or from 10 to 800 ppm by weight, or from 100 to 500 ppm by weight in terms of the converted value based on acrylic acid.

In some aspects, the suitable monomer that can be copolymerized with the ethylenically unsaturated monomer may include, but is not limited to acrylamide, methacrylamide, hydroxyethyl acrylate, dimethylaminoalkyl (meth)-acrylate, ethoxylated (meth)-acrylates, dimethylaminopropylacrylamide, or acrylamidopropyltrimethylammonium chloride. Such monomer may be present in a range of from 0 wt % to about 40 wt % of the copolymerized monomer.

When partially neutralized or completely neutralized acrylate salt is turned into the polymer in the particulate water absorbing agent following polymerization, the converted value based on acrylic acid may be determined through converting the partially neutralized or completely neutralized polyacrylate salt is assumed to be entirely the equimolar unneutralized polyacrylic acid.

The superabsorbent polymer of the invention also includes internal cross linking agents. The internal crosslinking agent has at least two ethylenically unsaturated double bonds or one ethylenically unsaturated double bond and one functional group which is reactive towards acid groups of the polymerizable unsaturated acid group containing monomers or several functional groups which are reactive towards acid groups can be used as the internal crosslinking component and which is present during the polymerization of the polymerizable unsaturated acid group containing monomers.

Examples of internal crosslinking agents include aliphatic unsaturated amides, such as methylenebisacryl- or -methacrylamide or ethylenebisacrylamide, and furthermore aliphatic esters of polyols or alkoxylated polyols with ethylenically unsaturated acids, such as di(meth)acrylates or tri(meth)acrylates of butanediol or ethylene glycol, polyglycols or trimethylolpropane, di- and triacrylate esters of trimethylolpropane which is preferably oxyalkylated, preferably ethoxylated, with 1 to 30 mol of alkylene oxide, acrylate and methacrylate esters of glycerol and pentaerythritol and of glycerol and pentaerythritol oxyethylated with preferably 1 to 30 mol of ethylene oxide and furthermore allyl compounds, such as allyl (meth)acrylate, alkoxylated allyl (meth)acrylate reacted with preferably 1 to 30 mol of ethylene oxide, triallyl cyanurate, triallyl isocyanurate, maleic acid diallyl ester, poly-allyl esters, vinyl trimethoxysilane, vinyl triethoxysilane, polysiloxane comprising at least two vinyl groups, tetraallyloxyethane, tetraallyloxyethane, triallylamine, tetraallylethylenediamine, diols, polyols, hydroxy allyl or acrylate compounds and allyl esters of phosphoric acid or phosphorous acid, and furthermore monomers which are capable of crosslinking, such as N-methylol compounds of unsaturated amides, such as of methacrylamide or acrylamide, and the ethers derived there from. Ionic crosslinkers such as multivalent metal salts may also be employed. Mixtures of the crosslinking agents mentioned can also be employed.

The internal crosslinking agents or their mixtures to be used according to the present invention are used in amounts of from about 0.001 wt % to about 5 wt % by weight or from about 0.2 wt % to about 3 wt % based on the total amount of the polymerizable unsaturated acid group containing monomer.

In another embodiment, the superabsorbent polymer may include from about 0.001 wt % to about 0.1 wt % based on the total amount of the polymerizable unsaturated acid group containing monomer of a second internal crosslinker which may comprise compositions comprising at least two ethylenically unsaturated double-bonds, for example, methylenebisacrylamide or -methacrylamide or ethylenebisacrylamide; additionally, esters of unsaturated mono- or polycarboxylic acids of polyols, such as, diacrylates or triacrylates, e.g., butanediol- or ethylene glycol diacrylate or -methacrylate; trimethylolpropane triacrylate, as well as their alkoxylated derivatives; additionally, allyl compounds, such as allyl (meth)acrylate, triallyl cyanurate, maleic acid diallyl ester, polyallyl ester, tetraallyloxyethane, di- and triallylamine, tetrallylethylenediamine, allyl esters of phosphoric acid or phosphorous acid. Moreover, compounds having at least one functional group reactive towards acid groups may also be used. Examples thereof include N-methylol compounds of amides, such as methacrylamide or acrylamide, and the ethers derived there from, as well as di- and polyglycidyl compounds.

The usual initiators, such as e.g. azo or peroxo compounds, redox systems or UV initiators, (sensitizers), and/or radiation are used for initiation of the free-radical polymerization. In some aspects, initiators can be used for initiation of the free-radical polymerization. Suitable initiators include, but are not limited to, azo or peroxo compounds, redox systems or ultraviolet initiators, sensitizers, and/or radiation.

The polymerization forms a superabsorbent polymer gel, which is granulated into superabsorbent polymer particles, or particulate superabsorbent polymer. The particulate superabsorbent polymer generally includes particle sizes ranging from about 50 μm to about 1000 μm, or from about 150 μm to about 850 μm. The present invention may include at least about 40 wt % of the particles having a particle size from about 300 μm to about 600 μm, at least about 50 wt % of the particles having a particle size from about 300 μm to about 600 μm, or at least about 60 wt % of the particles having a particle size from about 300 μm to about 600 μm as measured by screening through a U.S. standard 30 mesh screen and retained on a U.S. standard 50 mesh screen. In addition, the size distribution of the superabsorbent polymer particles of the present invention may include less than about 30% by weight of particles having a size greater than about 600 μm, and less than about 30% by weight of particles having a size of less than about 300 μm as measured using for example a RO-TAP® Mechanical Sieve Shaker Model B available from W. S. Tyler, Inc., Mentor Ohio. While particles are the used by way of example of the physical form of superabsorbent polymers, the invention is not limited to this form and is applicable to other forms such as fibers, foams, films, beads, rods and the like.

In one embodiment, the particulate superabsorbent polymer may then be surface treated with additional chemicals and treatments as set forth herein. In particular, the surface of the particulate superabsorbent polymer may be crosslinked, generally referred to as surface crosslinked, by the addition of a surface crosslinking agent and heat-treatment. In general, surface crosslinking is a process that is believed to increase the crosslink density of the polymer matrix in the vicinity of the particulate superabsorbent polymer surface with respect to the crosslinking density of the particle interior.

Desirable surface crosslinking agents may include chemicals with one or more functional groups that are reactive toward pendant groups of the polymer chains, typically the acid groups. Surface crosslinker agents may include compounds that comprise at least two functional groups which can react with functional groups of a polymer structure in a condensation reaction (condensation crosslinker), in an addition reaction or in a ring opening reaction. These compounds may include condensation crosslinkers such as, for example, diethylene glycol, triethylene glycol, polyethylene glycol, glycerine, polyglycerine, propylene glycol, diethanolamine, triethanolamine, polyoxypropylene, oxyethylene-oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one as well as 1,3-dioxolan-2-one. The amount of the surface crosslinking agent may be present in an amount of from about 0.01 wt % to about 5 wt % of the dry particulate superabsorbent polymer composition, and such as from about 0.1 wt % to about 3 wt %, and such as from about 0.1 wt % to about 1 wt % by weight, based on the weight of the dry particulate superabsorbent polymer composition.

After the particulate superabsorbent polymer have been brought into contact with the surface crosslinker or with the fluid comprising the surface crosslinker, the treated particulate superabsorbent polymer is heat treated which may include heating the coated particulate superabsorbent polymer to a temperature of from about 50 to about 300° C., or from about 75 to about 275° C., or from about 150 to about 250° C., and for a time of from about 5 to about 90 minutes dependent on the temperature, so that the outer region of the polymer structures is more strongly crosslinked compared to the inner region (i.e., surface crosslinking). The duration of the heat treatment is limited by the risk that the desired property profile of the polymer structures will be destroyed as a result of the effect of heat In one particular aspect of surface crosslinking, the particulate superabsorbent polymer is coated, or surface-treated, with an alkylene carbonate, such as ethylene carbonate, followed by heating to affect surface crosslinking, which can improve the surface crosslinking density and the gel strength characteristics of the particulate superabsorbent polymer. More specifically, the surface crosslinking agent is coated onto the particulate superabsorbent polymer by mixing the particulate superabsorbent polymer with an aqueous alcoholic solution of the alkylene carbonate surface crosslinking agent. The amount of alcohol in the aqueous alcoholic solution may be determined by the solubility of the alkylene carbonate and is kept as low as possible for various reasons, for instance, for protection against explosions. Suitable alcohols are methanol, isopropanol, ethanol, butanol, or butyl glycol, as well as mixtures of these alcohols. In some aspects, the solvent desirably is water, which typically is used in an amount of about 0.3% by weight to about 5.0 wt %, based on the weight of the dry particulate superabsorbent polymer composition. In still other aspects, the alkylene carbonate surface crosslinking agent may be applied from a powder mixture, for example, with an inorganic carrier material, such as silicone dioxide ($SiO_2$), or in a vapor state by sublimation of the alkylene carbonate.

To achieve the desired surface crosslinking properties, the alkylene carbonate should be distributed evenly on the particulate superabsorbent polymer. For this purpose, mixing is effected in suitable mixers known in the art, such as fluidized bed mixers, paddle mixers, rotary drum mixers, or twin-worm mixers. It is also possible to carry out the coating of the particulate superabsorbent polymer during one of the process steps in the production of the particulate superabsorbent polymer. In one particular aspect, a suitable process for this purpose is the inverse suspension polymerization process.

The heat treatment, which follows the coating treatment of the particulate superabsorbent polymer, may be carried out as follows. In general, the heat treatment is at a temperature of from about 100° C. to about 300° C. Lower temperatures are possible if highly reactive epoxide crosslinking agents are used. However, if an alkylene carbonate is used, then the thermal treatment is suitably at a temperature of from about 150° C. to about 250° C. In this particular aspect, the treatment temperature depends on the dwell time and the kind of alkylene carbonate. For example, at a temperature of about 150° C., the thermal treatment is carried out for one hour or longer. In contrast, at a temperature of about 250° C., a few minutes (e.g., from about 0.5 minutes to about 5 minutes) are sufficient to achieve the desired surface crosslinking properties. The thermal treatment may be carried out in conventional dryers or ovens known in the art.

In addition to surface crosslinking, the particulate superabsorbent polymer compositions may be further surface treated with other chemical compositions.

The absorbent polymers according to the invention can comprise from 0.01 wt % to about 5 wt % of a neutralized multivalent metal salt, based on the weight of the mixture, on the surface of the polymer. The neutralized multivalent metal salt is preferably water soluble. Examples of preferred metal cations include the cations of Al, Fe, Zr, Mg and Zn. Preferably, the metal cation has a valence of at least +3, with Al being most preferred. Mixtures of multivalent metal salts may also be employed.

The neutralized multivalent metal salt may include a chelating anion. Chelating anions suitable in this invention should be able to form a water-soluble complex with multivalent metal cations without compromising the performance enhancing effects from multivalent metal cations. Examples of preferred chelating anions are the anions of hydroxyl monocarboxylic acids such as lactic acid, glycolic acid, gluconic acid, or 3-hydroxypropionic acid. The molar ratio of organic acid to multivalent metal cation is preferably between about 0.5:1 to about 2:1 more preferably between about 0.75:1 to about 1.5:1.

The multivalent metal salt may be a neutralized aluminum salt in the form of an aqueous solution, which can be prepared by mixing an aluminum compound with an organic acid (salt), and adjusting the pH with a base or acid, using means well known to those skilled in the art. Examples of aluminum compounds which can be used in the present invention include: aluminum chloride, aluminum sulfate, aluminum nitrate, polyaluminum chloride, sodium aluminate, potassium aluminate, ammonium aluminate, aluminum hydroxide, and aluminum oxide.

The mixture of the aluminum compound with the organic acid (salt) can be acidic or basic. And the pH can be adjusted to the desired range with a basic or acidic material. Examples of the basic materials for pH adjustment include but not limited to sodium hydroxide, potassium hydroxide, ammonium hydroxide, sodium carbonate or sodium bicarbonate. Examples of the acidic materials for pH adjustment include but not limited to hydrochloride, sulfuric acid, methylsulfonic acid, or carbon dioxide in water. The acidic aluminum salts, such as aluminum chloride, aluminum sulfate, aluminum nitrate and polyaluminum chloride, or the basic aluminum salts, such as sodium aluminate, potassium aluminate and ammonium aluminate, may be used for pH adjustment as well.

The neutralized multivalent metal salt suitable in this invention has a pH from about 5 to about 9, or from about 5.5 to about 8, or from about 6 to about 7, in an aqueous solution at a concentration of at least about 5 percent by weight.

The neutralized multivalent metal salt may be added at various stages of surface treatment of the particulate superabsorbent polymer. For example, neutralized multivalent metal salt may be added to the surface crosslinking solution and applied to the particulate superabsorbent polymer along with the surface crosslinking solution; or the neutralized multivalent metal salt may be separately added from the surface crosslinking solution but as part of the surface crosslinking step; or the neutralized multivalent metal salt may be added after the surface crosslinking step.

The particulate superabsorbent polymer and the neutralized multivalent metal salt suitably are mixed by dry blending, or in solution, or in an aqueous solution using means well known to those skilled in the art. With dry blending, a binder may be employed in an amount which is sufficient to ensure that a substantially uniform mixture of the salt and the superabsorbent polymer is maintained. The binder may be water or a nonvolatile organic compound having a boiling point of at least 150° C. Examples of binders include water, polyols such as propylene glycol, glycerin and poly(ethylene glycol). The neutralized multivalent metal salt can be applied on the surface of superabsorbent polymer either before or after the surface crosslinking step.

In addition to the surface crosslinking agent, and the neutralized multivalent metal salt, the particulate superabsorbent polymer composition of the present invention may be surface treated with from 0 wt % to about 5 wt %, or from about 0.001 wt % to about 5 wt %, or from about 0.01 wt % to about 0.5 wt % based on the dry particulate superabsorbent polymer composition of a polymeric coating, such as a thermoplastic coating, or a cationic coating, or a combination of a thermoplastic coating and a cationic coating. In some particular aspects, the polymeric coating desirably is a polymer that may be in a solid, emulsion, suspension, colloidal, or solubilized state, or combinations thereof. Polymeric coatings suitable for this invention may include, but are not limited to, a thermoplastic coating having a thermoplastic melt temperature wherein the polymeric coating is applied to the particle surface coincident with or followed by a temperature of the treated superabsorbent polymer particle at about the thermoplastic melt temperature.

Examples of thermoplastic polymers include polyolefin, polyethylene, polyester, polyamide, polyurethane, styrene polybutadiene, linear low density polyethylene (LLDPE), ethylene acrylic acid copolymer (EAA), ethylene alkyl methacrylate copolymer (EMA), polypropylene (PP), maleated polypropylene, ethylene vinyl acetate copolymer (EVA), polyester, polyamide, and blends of all families of polyolefins, such as blends of PP, EVA, EMA, EEA, EBA, HDPE, MDPE, LDPE, LLDPE, and/or VLDPE, may also be advantageously employed. The term polyolefin as used herein is defined above. In particular aspects, maleated polypropylene is a preferred thermoplastic polymer for use in the present invention. A thermoplastic polymer may be functionalized to have additional benefits such as water solubility or dispersability.

Polymeric coatings of this invention may also include a cationic polymer. A cationic polymer as used herein refers to a polymer or mixture of polymers comprising a functional group or groups having a potential of becoming positively charged ions upon ionization in an aqueous solution. Suitable functional groups for a cationic polymer include, but are not limited to, primary, secondary, or tertiary amino groups, imino groups, imido groups, amido groups, and quaternary ammonium groups. Examples of synthetic cationic polymers include the salts or partial salts of poly(vinyl amines), poly(allylamines), poly(ethylene imine), poly(amino propanol vinyl ethers), poly(acrylamidopropyl trimethyl ammonium chloride), poly(diallyldimethyl ammonium chloride). Examples of natural-based cationic polymers include partially deacetylated chitin, chitosan, and chitosan salts. Synthetic polypeptides such as polyasparagins, polylysines, polyglutamines, and polyarginines are also suitable cationic polymers.

The absorbent polymers according to the invention may include from about 0 wt % to about 5 wt %, or from about 0.001 wt % to about 3 wt %, or from about 0.01 wt % to about 2 wt % based on the weight of the dry particulate superabsorbent polymer composition of water-insoluble, inorganic powder. Examples of insoluble, inorganic powders include silicon dioxide, silica, titanium dioxide, aluminum oxide, magnesium oxide, zinc oxide, talc, calcium phosphate, clays, diatomataceous earth, zeolites, bentonite, kaolin, hydrotalcite, activated clays, etc. The insoluble inorganic powder additive may be a single compound or a mixture of compounds selected from the above list. Examples of silica include fumed silica, precipitated silica, silicon dioxide, silicic acid, and silicates. In some particular aspects, microscopic noncrystalline silicon dioxide is desirable. Products include SIPERNAT® 22S and AEROSIL® 200 available from Evonik Corporation, Parsippany, N.J. In some aspects, the particle diameter of the inorganic powder can be 1,000 µm or smaller, such as 100 µm or smaller.

The superabsorbent polymer according to the invention may also include the addition of from 0 wt % to about 5 wt %, or from about 0.001 wt % to about 3 wt %, or from about 0.01 wt % to about 2 wt % based on the weight of the dry particulate superabsorbent polymer composition, of a surfactant to the polymer particle surface. It is preferred that these be added immediately prior to, during or immediately after the surface crosslinking step.

Examples of such surfactants include anionic, non-ionic, cationic and amphoteric surface active agents, such as fatty acid salts, coco amines and amides and their salts, alkylsulfuric ester salts, alkylbenzene sulfonic acid salts, dialkyl sulfo-succinate, alkyl phosphate salt, and polyoxyethylene alkyl sulfate salt; polyoxyethylene alkyl ether, polyoxyethylene alkyl phenol ether, polyoxyethylene fatty acid ester, sorbitan fatty acid ester, polyoxy sorbitan fatty acid ester, polyoxyethylene alkylamine, fatty acid esters, and oxyethyleneoxypropylene block polymer; alkyl amine salts, quaternary ammonium salts; and lauryl dimethylamine oxide. However, it is not necessary to restrict the surfactant to those mentioned above. Such surfactants may be used individually, or in combination.

The superabsorbent polymers may also include from 0 wt % to about 30 wt %, or from about 0.001 wt % to about 25 wt %, or from about 0.01 wt % to about 20 wt % based on the weight of the dry particulate superabsorbent polymer composition, of water-soluble polymers, such as partly or completely hydrolyzed polyvinyl acetate, polyvinylpyrrolidone, starch or starch derivatives, polyglycols or polyacrylic acids, preferably in polymerized-in form. The molecular weight of these polymers is not critical as long as they are water-soluble. Preferred water-soluble polymers are starch and polyvinyl alcohol. The preferred content of such water-soluble polymers in the absorbent polymer according to the invention is 0-30 wt %, or 0-5 wt %, based on the total amount of the dry particulate superabsorbent polymer composition. The water-soluble polymers, preferably synthetic polymers, such as polyvinyl alcohol, can also serve as a graft base for the monomers to be polymerized.

The superabsorbent polymers may also include from 0 wt % to about 5 wt %, or from about 0.001 wt % to about 3 wt %, or from about 0.01 wt % to about 2 wt % based on the weight of the dry particulate superabsorbent polymer composition, of dedusting agents, such as hydrophilic and hydrophobic dedusting agents such as those described in U.S. Pat. Nos. 6,090,875 and 5,994,440.

In some aspects, additional surface additives may optionally be employed with the superabsorbent polymer particles, such as odor-binding substances, such as cyclodextrins, zeolites, inorganic or organic salts, and similar materials; anti-caking additives, flow modification agents, surfactants, viscosity modifiers, and the like.

In some aspects, the particulate superabsorbent polymer compositions of the present invention may be, after a heat treatment step, treated with water so that the particulate superabsorbent polymer composition has water content of up to about 10% by weight of the superabsorbent polymer composition. This water may be added with one or more of the surface additives from above added to the superabsorbent polymer.

The particulate superabsorbent polymer composition according to the invention may be desirably prepared by various methods disclosed in the art including the following two methods. The particulate superabsorbent polymer composition may be prepared continuously or discontinuously in a large-scale industrial manner, the surface treatment including surface crosslinking being carried out according to the invention.

According to one method, the monomer is partially neutralized by either adding a caustic such as sodium hydroxide to the monomer or adding the monomer to the caustic. Then the partially neutralized monomer, such as acrylic acid, is converted into a gel by free-radical polymerization in aqueous solution in the presence of crosslinking agents and any further components, and the gel is comminuted, dried, ground, and sieved off to the desired particle size, thereby forming a particulate superabsorbent polymer. This polymerization can be carried out continuously or discontinuously.

For the present invention, the size of the high-capacity superabsorbent polymer composition particles is dependent on manufacturing processes including milling and sieving. It is well known to those skilled in the art that particle size distribution of the particulate superabsorbent polymer resembles a normal distribution or a bell shaped curve. It is also known that for various reasons, the normal distribution of the particle size distribution may be skewed in either direction.

According to another method to make particulate superabsorbent polymer, inverse suspension and emulsion polymerization can also be used for preparation of the products according to the invention. According to these processes, an aqueous, partly neutralized solution of monomer, such as acrylic acid, is dispersed in a hydrophobic, organic solvent with the aid of protective colloids and/or emulsifiers, and the polymerization is started by free radical initiators. The internal crosslinking agents may be either dissolved in the monomer solution and are metered in together with this, or are added separately and optionally during the polymerization. The addition of a water-soluble polymer as the graft base optionally takes place via the monomer solution or by direct introduction into the oily phase. The water is then removed azeotropically from the mixture, and the polymer is filtered off and optionally dried. Internal crosslinking can be carried out by polymerizing-in a polyfunctional crosslinking agent dissolved in the monomer solution and/or by reaction of suitable crosslinking agents with functional groups of the polymer during the polymerization steps.

The result of these methods is a particulate superabsorbent polymer, referred herein as a superabsorbent polymer preproduct. A superabsorbent polymer preproduct as used herein is produced by repeating all of the steps for making the superabsorbent polymer, up to and including drying the material, and coarse grinding in a crusher, and removing particles greater than about 850 μm and smaller than about 150 μm. The superabsorbent polymer preproduct is then surface treated including surface crosslinking to form the particulate superabsorbent polymer composition.

The particulate superabsorbent polymer composition of the present invention exhibits certain characteristics, or properties, as measured by Free Swell Gel Bed Permeability (GBP), Gel Bed Permeability under load at about 0.3 psi (0.3 psi GBP), Centrifuge Retention Capacity (CRC), and absorbency under load at about 0.9 psi (0.9 psi AUL). The Free Swell Gel Bed Permeability (GBP) Test is a measurement of the permeability of a swollen bed of superabsorbent material in Darcy (e.g., separate from the absorbent structure) under a confining pressure after what is commonly referred to as "free swell" conditions. In this context, the term "free swell" means that the superabsorbent material is allowed to swell without a swell restraining load upon absorbing test solution as will be described. Gel Bed Permeability under load at about 0.3 psi (0.3 psi GBP) is a measurement of the permeability of a swollen bed of superabsorbent material in Darcy (e.g., separate from the absorbent structure) under a confining pressure after what is commonly referred to as "0.3 psi" conditions. In this context, the term "0.3 psi" means that the superabsorbent material is allowed to swell under a confining pressure of 0.3 psi upon absorbing test solution as will be described.

The Centrifuge Retention Capacity (CRC) Test measures the ability of the particulate superabsorbent polymer composition to retain liquid therein after being saturated and subjected to centrifugation under controlled conditions. The resultant retention capacity is stated as grams of liquid retained per gram weight of the sample (g/g).

The Absorbency Under Load (AUL) Test measures the ability of the particulate superabsorbent polymer composition particles to absorb a 0.9 weight percent solution of sodium chloride in distilled water at room temperature (test solution) while the material is under a load of 0.9 psi.

All values of Centrifuge Retention Capacity, Absorbency Under Load and Gel Bed Permeability set forth herein are to be understood as being determined by the Centrifuge Retention Capacity Test, Absorbency Under Load Test, and Gel Bed Permeability Test as provided herein.

A particulate superabsorbent polymer composition made by a process of present invention may have a centrifuge retention capacity of from about 25 g/g to about 50 g/g, or from about 27 to about 35 g/g; and an absorbency under load at 0.9 psi of from about 16 g/g to about 24 g/g, or from about 18 to about 22 g/g, a free swell gel bed permeability of from about 20 to about 200 Darcy, and gel bed permeability under load at 0.3 psi of at least about 0.8 Darcy.

Surprisingly, the particulate superabsorbent polymer compositions according to the invention show a significant improvement in permeability, i.e. an improvement in the transportation of liquid in the swollen state, while maintaining high absorption and retention capacity.

In one embodiment of the present invention, the particulate superabsorbent polymer composition is a crosslinked polymer wherein the particulate superabsorbent polymer composition has a GBP of at least about $[5000\ e^{-0.18x}]$ Darcy, or at least about $[8,000\ e^{-0.18x}]$ Darcy where x is the numeric value of CRC. Such superabsorbent polymers exhibit a CRC from about 25 to 35 g/g, and a GBP at least about 20 Darcy, and AUL at 0.9 psi from about 18 g/g to 22 g/g. In another embodiment, the particulate superabsorbent polymer composition has a CRC from about 30 to about 35 g/g, and a GBP at least about 30 Darcy. In another embodiment, the particulate superabsorbent polymer composition has a GBP of at least about $[12,000\ e^{-0.18x}]$; or the GBP is at least about $[10,500\ e^{-0.18x}]$; or the particulate superabsorbent polymer composition has a CRC from about 27 to about 30 g/g, a GBP of at least about 40 Darcy, and an absorbency under load at 0.9 psi (AUL) from about 18 g/g to 22 g/g.

The particulate superabsorbent polymer compositions according to the present invention can be employed in many absorbent articles including sanitary towels, diapers, or wound coverings, and they have the property that they rapidly absorb large amounts of menstrual blood, urine, or other body fluids. Since the agents according to the invention retain the absorbed liquids even under pressure and are also capable of distributing further liquid within the construction in the swollen state, they are more desirably employed in higher concentrations, with respect to the hydrophilic fiber material, such as fluff, when compared to conventional current superabsorbent compositions. They are also suitable for use as a homogeneous superabsorber layer without fluff content within the diaper construction, as a result of which particularly thin articles are possible. The polymers are furthermore suitable for use in hygiene articles (incontinence products) for adults.

Absorbent articles generally include a core, which may include from about 60 to 100 wt % of particulate superabsorbent polymer composition, or may be a fibrous web including 0 to about 40 wt % of fibrous web such as cellulose, or the core may include at least about 90 wt % particulate superabsorbent polymer composition and up to 10 wt % of cellulose fiber, or may include at least about 95 wt % of particulate superabsorbent polymer composition and up to about 5 wt % of nanofiber fibers wherein the nanofibers fibers include fibers having a diameter of less than about 10 μm, or less than about 1 μm.

Absorbent articles, like diapers, may include, (a) a liquid pervious topsheet; (b) a liquid impervious backsheet; (c) a core positioned between (a) and (b) and comprising about 10% to 100%, and preferably about 50 wt % to about 100 wt %, of the particulate superabsorbent polymer composition, and 0% to 90% by weight of hydrophilic fiber material; (d) optionally a tissue layer positioned directly above and below said core (c); and (e) optionally an acquisition The preparation of laminates in the broadest sense, and of extruded and coextruded, wet- and dry-bonded, as well as subsequently bonded, structures are possible as further preparation processes. A combination of these possible processes with one another is also possible.

The polymers according to the invention are also employed in absorbent articles that are suitable for further uses. In particular, the polymers of this invention can be used in absorbent compositions for absorbents for water or aqueous liquids, preferably in constructions for absorption of body fluids, in foamed and non-foamed sheet-like structures, in packaging materials, in constructions for plant growing, as soil improvement agents or as active compound carriers. For this, they are processed to a web by mixing with paper or fluff or synthetic fibers or by distributing the superabsorbent polymers between substrates of paper, fluff or non-woven textiles or by processing into carrier materials.

They are further suited for use in absorbent compositions such as wound dressings, packaging, agricultural absorbents, food trays and pads, and the like.

Surprisingly, the superabsorbent polymers according to the invention show a significant improvement in permeability, i.e. an improvement in the transportation of liquid in the swollen state, while maintaining high absorption and retention capacity.

Test Procedures

Centrifuge Retention Capacity Test (CRC).

The CRC Test measures the ability of the particulate superabsorbent polymer composition to retain liquid therein after being saturated and subjected to centrifugation under controlled conditions. The resultant retention capacity is stated as grams of liquid retained per gram weight of the sample, (g/g). The sample to be tested is prepared from particles that are pre-screened through a U.S. standard 30-mesh screen and retained on a U.S. standard 50-mesh screen. As a result, the particulate superabsorbent polymer composition sample comprises particles sized in the range of about 300 to about 600 microns. The particles can be pre-screened by hand or automatically.

The retention capacity is measured by placing about 0.16 grams of the pre-screened particulate superabsorbent polymer composition sample into a water-permeable bag that will contain the sample while allowing a test solution (0.9 weight percent sodium chloride in distilled water) to be freely absorbed by the sample. A heat-sealable tea bag material, such as that available from Dexter Corporation (having a place of business in Windsor Locks, Conn., U.S.A.) as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals are about 0.25 inches inside the edge of the material. After the sample is placed in the pouch, the remaining open edge of the pouch is also heat-sealed. Empty bags are also made to serve as controls. Three samples are prepared for each particulate superabsorbent polymer composition to be tested.

The sealed bags are submerged in a pan containing the test solution at about 23° C., making sure that the bags are held down until they are completely wetted. After wetting, the particulate superabsorbent polymer composition samples remain in the solution for about 30 minutes, at which time they are removed from the solution and temporarily laid on a non-absorbent flat surface.

The wet bags are then placed into the basket wherein the wet bags are separated from each other and are placed at the outer circumferential edge of the basket, wherein the basket is of a suitable centrifuge capable of subjecting the samples to a g-force of about 350. One suitable centrifuge is a CLAY ADAMS DYNAC II, model #0103, having a water collection basket, a digital rpm gauge, and a machined drainage basket adapted to hold and drain the flat bag samples. Where multiple samples are centrifuged, the samples are placed in opposing positions within the centrifuge to balance the basket when spinning. The bags (including the wet, empty bags) are centrifuged at about 1,600 rpm (e.g., to achieve a target g-force of about 350 g force with a variance from about 240 to about 360 g force), for 3 minutes. G force is defined as an unit of inertial force on a body that is subjected to rapid acceleration or gravity, equal to 32 ft/sec$^2$ at sea level. The bags are removed and weighed, with the empty bags (controls) being weighed first, followed by the bags containing the particulate superabsorbent polymer composition samples. The amount of solution retained by the particulate superabsorbent polymer composition sample, taking into account the solution retained by the bag itself, is the centrifuge retention capacity (CRC) of the superabsorbent polymer, expressed as grams of fluid per gram of superabsorbent polymer. More particularly, the retention capacity is determined by the following equation:

$$CRC = \frac{[\text{sample bag after centrifuge} - \text{empty bag after centrifuge} - \text{dry sample weight}]}{\text{dry sample weight}}$$

The three samples are tested, and the results are averaged to determine the CRC of the particulate superabsorbent polymer composition.

Free-Swell Gel Bed Permeability Test (FSGBP)

Figure 2:
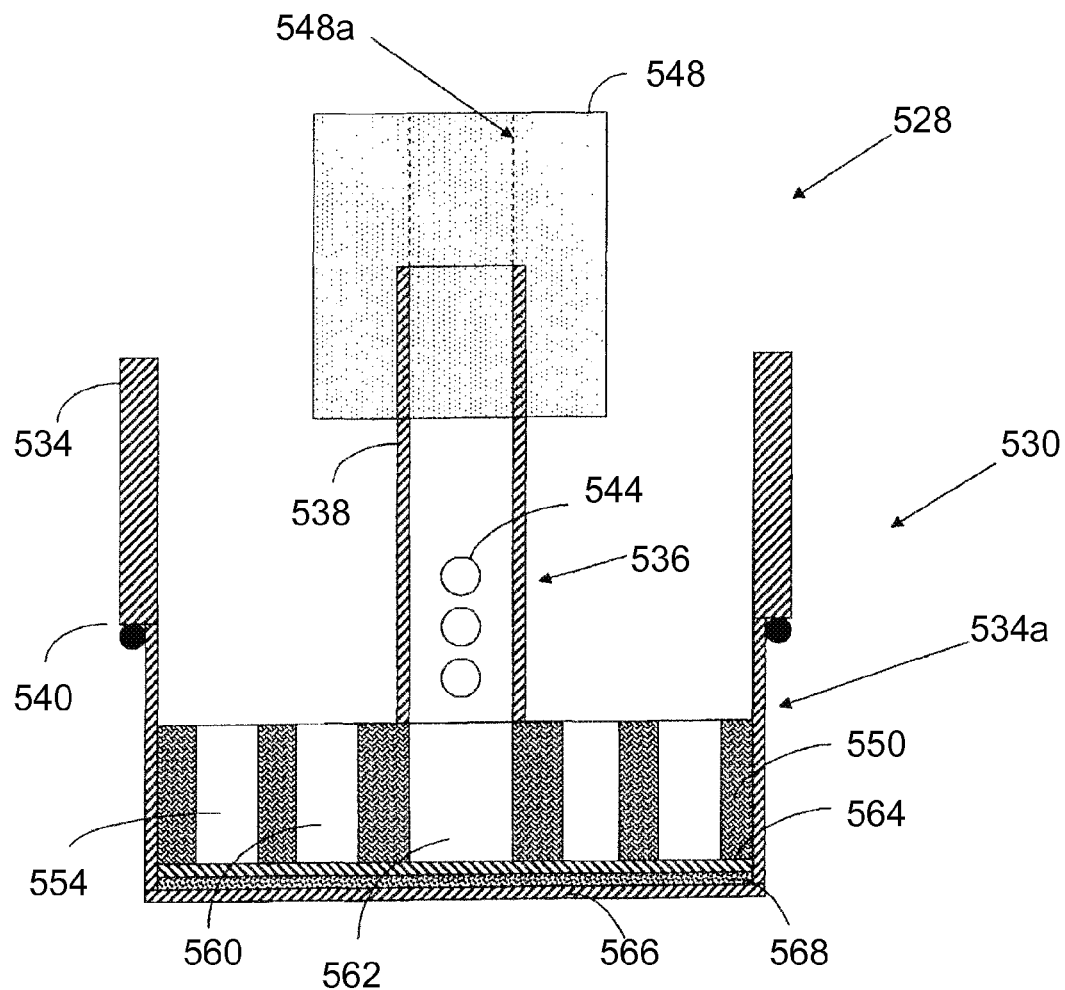
FIG. 2 is a cross-sectional side view of a cylinder/cup assembly employed in the Free Swell Gel Bed Permeability Test apparatus shown in FIG. 1.
Figure 3:
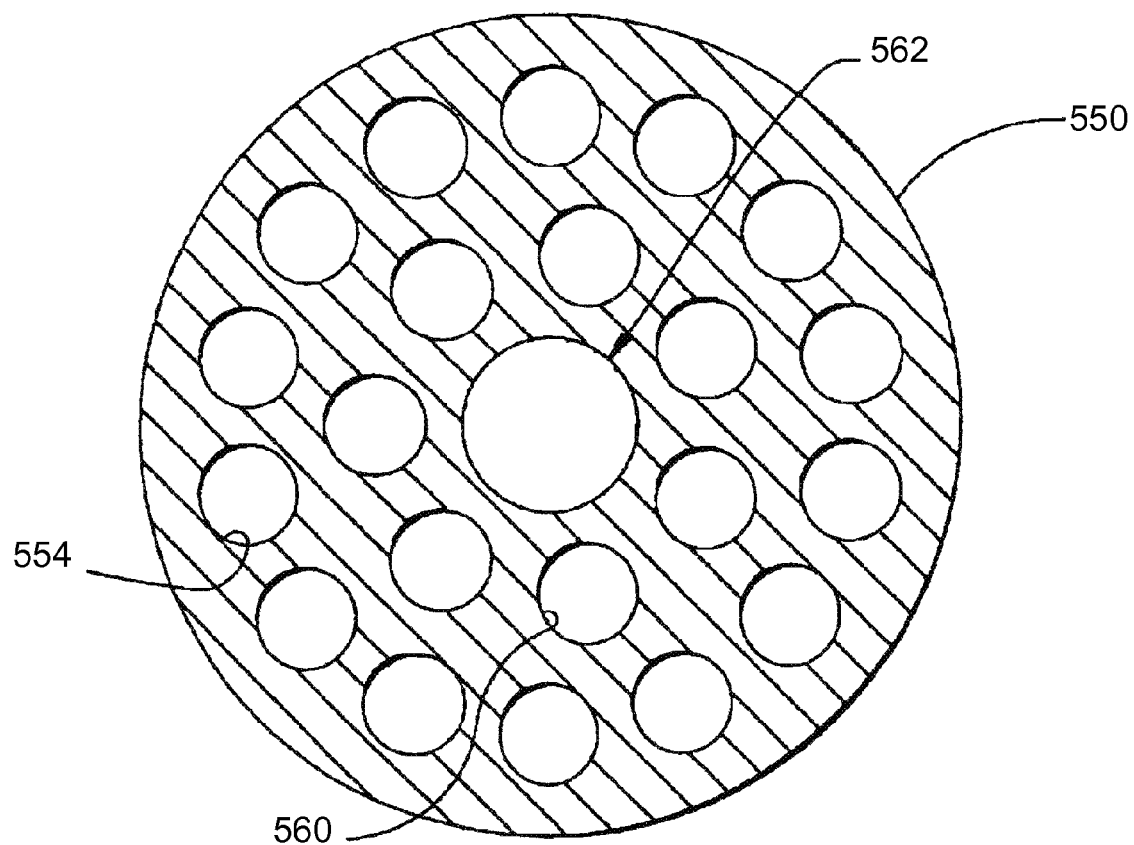
FIG. 3 is a top view of a plunger employed in the Free Swell Gel Bed Permeability Test apparatus shown in FIG. 1.

As used herein, the Free-Swell Gel Bed Permeability Test, also referred to as the Gel Bed Permeability Under 0 psi Swell Pressure Test (FSGBP), determines the permeability of a swollen bed of gel particles (e.g., such as the particulate superabsorbent polymer composition, or the particulate superabsorbent polymer prior to being surface treated), under what is commonly referred to as "free swell" conditions. The term "free swell" means that the gel particles are allowed to swell without a restraining load upon absorbing test solution as will be described. A suitable apparatus for conducting the Gel Bed Permeability Test is shown in FIGS. 1, 2, and 3 and indicated generally as 500. The test apparatus assembly 528 comprises a sample container, generally indicated at 530, and a plunger, generally indicated at 536. The plunger comprises a shaft 538 having a cylinder hole bored down the longitudinal axis and a head 550 positioned at the bottom of the shaft. The shaft hole 562 has a diameter of about 16 mm. The plunger head is attached to the shaft, such as by adhesion. Twelve holes 544 are bored into the radial axis of the shaft, three positioned at every 90 degrees having diameters of about 6.4 mm. The shaft 538 is machined from a LEXAN rod or equivalent material and has an outer diameter of about 2.2 cm and an inner diameter of about 16 mm.

The plunger head 550 has a concentric inner ring of seven holes 560 and an outer ring of 14 holes 554, all holes having a diameter of about 8.8 millimeters as well as a hole of about 16 mm aligned with the shaft. The plunger head 550 is machined from a LEXAN rod or equivalent material and has a height of approximately 16 mm and a diameter sized such that it fits within the cylinder 534 with minimum wall clearance but still slides freely. The total length of the plunger head 550 and shaft 538 is about 8.25 cm, but can be machined at the top of the shaft to obtain the desired mass of the plunger 536. The plunger 536 comprises a 100 mesh stainless steel cloth screen 564 that is biaxially stretched to tautness and attached to the lower end of the plunger 536. The screen is attached to the plunger head 550 using an appropriate solvent that causes the screen to be securely adhered to the plunger head 550. Care must be taken to avoid excess solvent migrating into the open portions of the screen and reducing the open area for liquid flow. Acrylic adhesive, Weld-On #4, from IPS Corporation (having a place of business in Gardena, Calif., USA) is a suitable adhesive.

The sample container 530 comprises a cylinder 534 and a 400 mesh stainless steel cloth screen 566 that is biaxially stretched to tautness and attached to the lower end of the cylinder 534. The screen is attached to the cylinder using an appropriate solvent that causes the screen to be securely adhered to the cylinder. Care must be taken to avoid excess solvent migrating into the open portions of the screen and reducing the open area for liquid flow. Acrylic adhesive, Weld-On #4, from IPS Corporation is a suitable adhesive. A gel particle sample, indicated as 568 in FIG. 2, is supported on the screen 566 within the cylinder 534 during testing.

The cylinder 534 may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm and a height of approximately 7.95 cm. A step is machined into the outer diameter of the cylinder 534 such that a region 534a with an outer diameter of 66 mm exists for the bottom 31 mm of the cylinder 534. An o-ring 540 which fits the diameter of region 534a may be placed at the top of the step.

The annular weight 548 has a counter-bored hole about 2.2 cm in diameter and 1.3 cm deep so that it slips freely onto the shaft 538. The annular weight also has a thru-bore 548a of about 16 mm. The annular weight 548 can be made from stainless steel or from other suitable materials resistant to corrosion in the presence of the test solution, which is 0.9 weight percent sodium chloride solution in distilled water. The combined weight of the plunger 536 and annular weight 548 equals approximately 596 grams (g), which corresponds to a pressure applied to the sample 568 of about 0.3 pounds per square inch (psi), or about 20.7 dynes/cm$^2$ (2.07 kPa), over a sample area of about 28.27 cm$^2$.

When the test solution flows through the test apparatus during testing as described below, the sample container 530 generally rests on a weir 600. The purpose of the weir is to divert liquid that overflows the top of the sample container 530 and diverts the overflow liquid to a separate collection device 601. The weir can be positioned above a scale 602 with a beaker 603 resting on it to collect saline solution passing through the swollen sample 568.

To conduct the Gel Bed Permeability Test under "free swell" conditions, the plunger 536, with the weight 548 seated thereon, is placed in an empty sample container 530 and the height from the top of the weight 548 to the bottom of the sample container 530 is measured using a suitable gauge accurate to 0.01 mm. The force the thickness gauge applies during measurement should be as low as possible, preferably less than about 0.74 Newtons. It is important to measure the height of each empty sample container 530, plunger 536, and weight 548 combination and to keep track of which plunger 536 and weight 548 is used when using multiple test apparatus. The same plunger 536 and weight 548 should be used for measurement when the sample 568 is later swollen following saturation. It is also desirable that the base that the sample cup 530 is resting on is level, and the top surface of the weight 548 is parallel to the bottom surface of the sample cup 530.

The sample to be tested is prepared from the particulate superabsorbent polymer composition, which is prescreened through a U.S. standard 30 mesh screen and retained on a U.S. standard 50 mesh screen. As a result, the test sample comprises particles sized in the range of about 300 to about 600 microns. The superabsorbent polymer particles can be pre-screened with, for example, a RO-TAP Mechanical Sieve Shaker Model B available from W. S. Tyler, Inc., Mentor Ohio. Sieving is conducted for 10 minutes. Approximately 2.0 grams of the sample is placed in the sample container 530 and spread out evenly on the bottom of the sample container. The container, with 2.0 grams of sample in it, without the plunger 536 and weight 548 therein, is then submerged in the 0.9% saline solution for a time period of about 60 minutes to saturate the sample and allow the sample to swell free of any restraining load. During saturation, the sample cup 530 is set on a mesh located in the liquid reservoir so that the sample cup 530 is raised slightly above the bottom of the liquid reservoir. The mesh does not inhibit the flow of saline solution into the sample cup 530. A suitable mesh can be obtained as part number 7308 from Eagle Supply and Plastic, having a place of business in Appleton, Wis., U.S.A. Saline does not fully cover the superabsorbent polymer composition particles, as would be evidenced by a perfectly flat saline surface in the test cell. Also, saline depth is not allowed to fall so low that the surface within the cell is defined solely by swollen superabsorbent, rather than saline.

At the end of this period, the plunger 536 and weight 548 assembly is placed on the saturated sample 568 in the sample container 530 and then the sample container 530, plunger 536, weight 548, and sample 568 are removed from the solution. After removal and before being measured, the sample container 530, plunger 536, weight 548, and sample 568 are to remain at rest for about 30 seconds on a suitable flat, large grid non-deformable plate of uniform thickness. The thickness of the saturated sample 568 is determined by again measuring the height from the top of the weight 548 to the bottom of the sample container 530, using the same thickness gauge used previously provided that the zero point is unchanged from the initial height measurement. The sample container 530, plunger 536, weight 548, and sample 568 may be placed on a flat, large grid non-deformable plate of uniform thickness that will provide for drainage. The plate has an overall dimension of 7.6 cm by 7.6 cm, and each grid has a cell size dimension of 1.59 cm long by 1.59 cm wide by 1.12 cm deep. A suitable flat, large grid non-deformable plate material is a parabolic diffuser panel, catalogue number 1624K27, available from McMaster Can Supply Company, having a place of business in Chicago, Ill., U.S.A., which can then be cut to the proper dimensions. This flat, large mesh non-deformable plate must also be present when measuring the height of the initial empty assembly. The height measurement should be made as soon as practicable after the thickness gauge is engaged. The height measurement obtained from measuring the empty sample container 530, plunger 536, and weight 548 is subtracted from the height measurement obtained after saturating the sample 568. The resulting value is the thickness, or height "H" of the swollen sample.

The permeability measurement is initiated by delivering a flow of the 0.9% saline solution into the sample container 530 with the saturated sample 568, plunger 536, and weight 548 inside. The flow rate of test solution into the container is adjusted to cause saline solution to overflow the top of the cylinder 534 thereby resulting in a consistent head pressure equal to the height of the sample container 530. The test solution may be added by any suitable means that is sufficient to ensure a small, but consistent amount of overflow from the top of the cylinder, such as with a metering pump 604. The overflow liquid is diverted into a separate collection device 601. The quantity of solution passing through the sample 568 versus time is measured gravimetrically using the scale 602 and beaker 603. Data points from the scale 602 are collected every second for at least sixty seconds once the overflow has begun. Data collection may be taken manually or with data collection software. The flow rate, Q, through the swollen sample 568 is determined in units of grams/second (g/s) by a linear least-square fit of fluid passing through the sample 568 (in grams) versus time (in seconds).

Permeability in $cm^2$ is obtained by the following equation:

$$K=[Q*H*\mu]/[A*\rho*P]$$

where K=Permeability ($cm^2$), Q=flow rate (g/sec), H=height of swollen sample (cm), $\mu$=liquid viscosity (poise) (approximately one centipoise for the test solution used with this Test), A=cross-sectional area for liquid flow (28.27 $cm^2$ for the sample container used with this Test), $\rho$=liquid density ($g/cm^3$) (approximately one $g/cm^3$, for the test solution used with this Test) and P=hydrostatic pressure ($dynes/cm^2$) (normally approximately 7,797 $dynes/cm^2$). The hydrostatic pressure is calculated from $P=\rho*g*h$, where $\rho$=liquid density ($g/cm^3$), g=gravitational acceleration, nominally 981 $cm/sec^2$, and h=fluid height, e.g., 7.95 cm for the Gel Bed Permeability Test described herein.

A minimum of two samples is tested and the results are averaged to determine the gel bed permeability of the sample of particulate superabsorbent polymer composition.

Gel Bed Permeability Under Load at 0.3 psi Test (GBP 0.3 psi)

Gel Bed Permeability Under Load at 0.3 psi is tested in the manner as Free-swell Gel Bed Permeability Test, except that the plunger 536 and weight 548 are placed on the dry sample 568 in the sample container 530 before the assembly is submerged in the 0.9% saline solution.

Absorbency Under Load Test (AUL (0.9 psi))

The Absorbency Under Load (AUL) Test measures the ability of the particulate superabsorbent polymer composition to absorb a 0.9 weight percent solution of sodium chloride in distilled water at room temperature (test solution) while the material is under a 0.9 psi load. The apparatus for testing AUL consists of:

An AUL assembly including a cylinder, a 4.4 g piston, and a standard 317 gm weight. The components of this assembly are described in additional detail below.

A flat-bottomed square plastic tray that is sufficiently broad to allow the glass frits to lay on the bottom without contact with the tray walls. A plastic tray that is 9" by 9" (22.9 cm×22.9 cm), with a depth of 0.5 to 1" (1.3 cm to 2.5 cm) is commonly used for this test method.

A 9 cm diameter sintered glass frit with a 'C' porosity (25-50 microns).

This frit is prepared in advance through equilibration in saline (0.9% sodium chloride in distilled water, by weight). In addition to being washed with at least two portions of fresh saline, the frit must be immersed in saline for at least 12 hours prior to AUL measurements.

Whatman Grade 1, 9 cm diameter filter paper circles.

A supply of saline (0.9% sodium chloride in distilled water, by weight).

Figure 4:
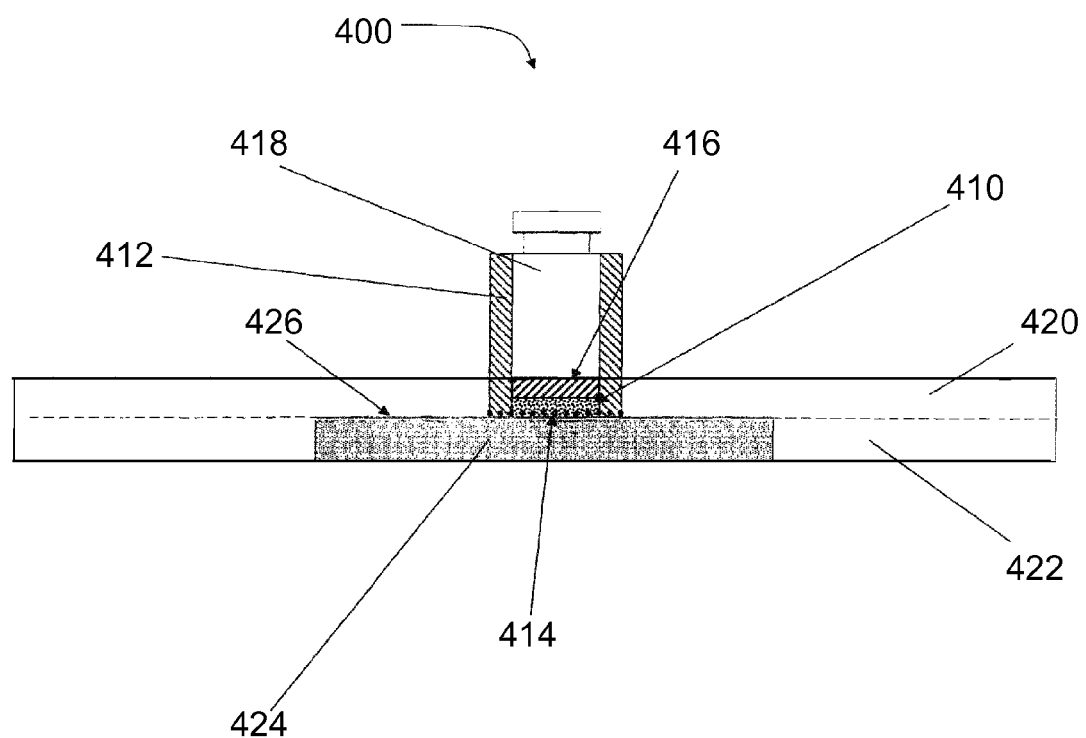
FIG. 4 is a side view of the test apparatus employed for the Absorbency Under Load Test.

Referring to FIG. 4, the cylinder 412 of the AUL assembly 400 used to contain the particulate superabsorbent polymer composition 410 is made from one-inch (2.54 cm) inside diameter thermoplastic tubing machined-out slightly to be sure of concentricity. After machining, a 400 mesh stainless steel wire cloth 414 is attached to the bottom of the cylinder 412 by heating the steel wire cloth 414 in a flame until red hot, after which the cylinder 412 is held onto the steel wire cloth until cooled. A soldering iron can be utilized to touch up the seal if unsuccessful or if it breaks. Care must be taken to maintain a flat smooth bottom and not distort the inside of the cylinder 412.

The 4.4 g piston (416) is made from one-inch diameter solid material (e.g., PLEXIGLAS®) and is machined to closely fit without binding in the cylinder 412.

A standard 317 gm weight 418 is used to provide a 62,053 dyne/cm$^2$ (about 0.9 psi) restraining load. The weight is a cylindrical, 1 inch (2.5 cm) diameter, stainless steel weight that is machined to closely fit without binding in the cylinder.

Unless specified otherwise, a sample 410 corresponding to a layer of at least about 300 gsm. (0.16 g) of superabsorbent polymer composition particles is utilized for testing the AUL. The sample 410 is taken from superabsorbent polymer composition particles that are pre-screened through U.S. standard #30 mesh and retained on U.S. std. #50 mesh. The superabsorbent polymer composition particles can be pre-screened with, for example, a RO-TAP® Mechanical Sieve Shaker Model B available from W. S. Tyler, Inc., Mentor Ohio. Sieving is conducted for about 10 minutes.

The inside of the cylinder 412 is wiped with an antistatic cloth prior to placing the superabsorbent polymer composition particles 410 into the cylinder 412.

The desired amount of the sample of sieved particulate superabsorbent polymer composition 410 (about 0.16 g) is weighed out on a weigh paper and evenly distributed on the wire cloth 414 at the bottom of the cylinder 412. The weight of the particulate superabsorbent polymer composition in the bottom of the cylinder is recorded as 'SA,' for use in the AUL calculation described below. Care is taken to be sure no particulate superabsorbent polymer composition cling to the wall of the cylinder. After carefully placing the 4.4 g piston 412 and 317 g weight 418 on the superabsorbent polymer composition particles 410 in the cylinder 412, the AUL assembly 400 including the cylinder, piston, weight, and particulate superabsorbent polymer composition particles is weighed, and the weight is recorded as weight 'A'.

A sintered glass frit 424 (described above) is placed in the plastic tray 420, with saline 422 added to a level equal to that of the upper surface of the glass frit 424. A single circle of filter paper 426 is placed gently on the glass frit 424, and the AUL assembly 400 with the particulate superabsorbent polymer composition 410 is then placed on top of the filter paper 426. The AUL assembly 400 is then allowed to remain on top of the filter paper 426 for a test period of one hour, with attention paid to keeping the saline level in the tray constant.

At the end of the one hour test period, the AUL apparatus is then weighed, with this value recorded as weight 'B.'

The AUL (0.9 psi) is calculated as follows:

$$AUL(0.9\ psi) = (B - A)/SA$$

wherein
A=Weight of AUL Unit with dry SAP
B=Weight of AUL Unit with SAP after 60 minutes absorption
SA=Actual SAP weight A minimum of two tests is performed and the results are averaged to determine the AUL value under 0.9 psi load. The particulate superabsorbent polymer composition samples are tested at about 23° C. and about 50% relative humidity.

EXAMPLES

The following SAP Preproduct, Comparative Examples 1-7, and Examples 1-14 are provided to illustrate the inventions of products including particulate superabsorbent polymer composition, an absorbent article, and processes to make particulate superabsorbent polymer composition as set forth in the claims, and do not limit the scope of the claims. Unless otherwise stated all parts, and percentages are based on the dry particulate superabsorbent polymer composition.

SAP Preproduct A

A superabsorbent polymer may be made in the following way. Into a polyethylene vessel equipped with an agitator and cooling coils was added, 2.0 kg of 50% NaOH and 3.32 kg of distilled water and cooled to 20° C. 0.8 kg of glacial acrylic acid was then added to the caustic solution and the solution again cooled to 20° C. 4.8 g of polyethylene glycol monoallylether acrylate, 4.8 g of ethoxylated trimethylol propane triacrylate SARTOMER® 454 product, and 1.6 kg of glacial acrylic acid were added to the first solution, followed by cooling to 4-6° C. Nitrogen was bubbled through the monomer solution for about 5 minutes. The monomer solution was then discharged into a rectangular tray. 80 g of 1% by weight of $H_2O_2$ aqueous solution, 120 g of 2 wt % aqueous sodium persulfate solution, and 72 g of 0.5 wt % aqueous sodium erythorbate solution was added into the monomer solution to initiate polymerization reaction. The agitator was stopped and the initiated monomer was allowed to polymerize for 20 minutes.

A particulate superabsorbent polymer may be prepared as follows. The resulting hydrogel was chopped and extruded with a Hobart 4M6 commercial extruder, followed by drying in a Procter & Schwartz Model 062 forced air oven at 175° C. for 12 minutes with up flow and 6 minutes with down flow air on a 20 inch×40 inch perforated metal tray to a final product moisture level of less than 5 wt %. The dried material was coarse-ground in a Prodeva Model 315-S crusher, milled in an MPI 666-F three-stage roller mill and sieved with a Minox MTS 600DS3V to remove particles greater than 850 µm and smaller than 150 µm. The obtained SAP Preproduct A was then subjected to the surface modification as described in the following examples and comparative examples.

Comparative particulate superabsorbent polymer composition examples 1-7 may be prepared in the following manner.

Comparative Example 1

1.84 g of aluminum sulfate hydrate (technical grade, commercially available from Fisher Scientific) was dissolved in 8 g of deionized water. The pH of the solution was tested as 2.8. Ethylene carbonate (2 g) was dissolved in the aluminum sulfate solution and the resulting mixture was applied on the surface of 200 g of SAP preproduct A using a finely atomized spray from a Paasche VL sprayer while the SAP particles were fluidized in air and continuously mixed. The coated material was then heated in a convection oven at 185° C. for 25 minutes for surface crosslinking. The comparative particulate superabsorbent polymer composition was then sieved with 20/100 mesh US standard sieves to remove particles greater than 850 μm and smaller than 150 μm.

Comparative Example 2

1.82 g of aluminum lactate (commercially available from Sigma-Aldrich) was dissolved in 8 g of deionized water. The pH of the solution was tested as 3.7. Ethylene carbonate (2 g) was dissolved in the aluminum lactate solution and the resulting mixture was applied on the surface of 200 g of SAP preproduct A using a finely atomized spray from a Paasche VL sprayer while the SAP particles were fluidized in air and continuously mixed. The coated material was then heated in a convection oven at 185° C. for 35 minutes for surface crosslinking. The comparative particulate superabsorbent polymer composition was then sieved with 20/100 mesh US standard sieves to remove particles greater than 850 μm and smaller than 150 μm.

Comparative Example 3

1.84 g of aluminum sulfate hydrate (technical grade, commercially available from Fisher Scientific) and 0.59 g of lactic acid (88%, commercially available from Archer Daniels Midland Company (ADM), Decatur, Ill. 62526, U.S.A.) were dissolved in 8 g of deionized water. The pH of the solution was tested as 1.0. Ethylene carbonate (2 g) was dissolved in the above solution and the resulting mixture was applied on the surface of 200 g of SAP preproduct A using a finely atomized spray from a Paasche VL sprayer while the SAP particles were fluidized in air and continuously mixed. The coated material was then heated in a convection oven at 185° C. for 35 minutes for surface crosslinking The comparative particulate superabsorbent polymer composition was then sieved with 20/100 mesh US standard sieves to remove particles greater than 850 μm and smaller than 150 μm.

Comparative Example 4

1.84 g of aluminum sulfate hydrate (technical grade, commercially available from Fisher Scientific) and 0.76 g of sodium lactate (commercially available from Sigma-Aldrich) were dissolved in 8 g of deionized water. The pH of the solution was tested as 2.8. Ethylene carbonate (2 g) was dissolved in the above solution and the resulting mixture was applied on the surface of 200 g of SAP preproduct A using a finely atomized spray from a Paasche VL sprayer while the SAP particles were fluidized in air and continuously mixed. The coated material was then heated in a convection oven at 185° C. for 35 minutes for surface crosslinking. The comparative particulate superabsorbent polymer composition was then sieved with 20/100 mesh US standard sieves to remove particles greater than 850 μm and smaller than 150 μm.

Comparative Example 5

0.48 g of sodium aluminate (commercially available from Sigma-Aldrich) was dissolved in 8 g of deionized water. The pH of the solution was tested as 14. Ethylene carbonate (2 g) was dissolved in the above solution and the resulting mixture was applied on the surface of 200 g of SAP preproduct A using a finely atomized spray from a Paasche VL sprayer while the SAP particles were fluidized in air and continuously mixed. The coated material was then heated in a convection oven at 185° C. for 50 minutes for surface crosslinking. The comparative particulate superabsorbent polymer composition was then sieved with 20/100 mesh US standard sieves to remove particles greater than 850 μm and smaller than 150 μm.

Comparative Example 6

3.44 g of aluminum lactate (commercially available from Sigma-Aldrich) was dissolved in 15.28 g of deionized water. 1.45 gram of sodium hydroxide solution (50% in water) was added into the solution to increase the pH to 6.4. The molar ratio of lactate to aluminum of the solution was 3:1. Ethylene carbonate (2 g) was dissolved in 10.08 g of the above solution and the resulting mixture was applied on the surface of 200 g of SAP preproduct A using a finely atomized spray from a Paasche VL sprayer while the SAP particles were fluidized in air and continuously mixed. The coated material was then heated in a convection oven at 185° C. for 45 minutes for surface crosslinking. The comparative particulate superabsorbent polymer composition was then sieved with 20/100 mesh US standard sieves to remove particles greater than 850 μm and smaller than 150 μm.

Comparative Example 7

To a 600-ml beaker was added 160 g of water, 40 g of sodium hydroxide solution (50% wt/wt in water), and 41 g of sodium aluminate (commercially available from Sigma-Aldrich). The mixture was stirred to give a clear solution. A solution of citric acid monohydrate (105 g, commercially available from Sigma-Aldrich) in 150 g of water was added into the beaker while the beaker was cooled in an ice bath. The resulting mixture was a clear solution with a pH value of 7. The molar ratio of citrate to aluminum of the solution was about 1:1.

4.0 g of aluminum citrate solution, 2.0 g of ethylene carbonate, and 4.0 g of deionized water were mixed to give a clear solution. The resulting mixture was applied on the surface of 200 g of SAP preproduct A using a finely atomized spray from a Paasche VL sprayer while the SAP particles were fluidized in air and continuously mixed. The coated material was then heated in a convection oven at 185° C. for 40 minutes for surface crosslinking. The comparative particulate superabsorbent polymer composition was then sieved with 20/100 mesh US standard sieves to remove particles greater than 850 μm and smaller than 150 μm.

Particulate superabsorbent polymer compositions of the present invention may be made in the following manner as set forth in Examples 1-14.

Example 1

To a 100-ml beaker were added 4.09 g of lactic acid (88%, commercially available from ADM) and 16.57 g of water. The beaker was cooled in an ice bath and 10.15 g of sodium hydroxide solution (50% wt/wt in water) wad added in slowly. The mixture was stirred to give a clear solution. A solution of aluminum sulfate hydrate (24.78 g, 48% wt/wt in water) was added into the beaker while the beaker was cooled in an ice bath. The resulting mixture was a clear solution with a pH value of 6.5. The molar ratio of lactate to aluminum of the solution was about 1:1.

11.12 g of the aluminum salt solution obtained herein, 2.0 g of ethylene carbonate, and 1 g of deionized water were mixed to give a clear solution. The resulting mixture was applied on the surface of 200 g of SAP preproduct A using a finely atomized spray from a Paasche VL sprayer while the SAP particles were fluidized in air and continuously mixed. The coated material was then heated in a convection oven at 185° C. for 35 minutes for surface crosslinking. The particulate superabsorbent polymer composition was then sieved with 20/100 mesh US standard sieves to remove particles greater than 850 μm and smaller than 150 μm.

Example 2

To a 1000-ml beaker were added 49 g of lactic acid (88%, commercially available from ADM) and 161.5 g of water. The beaker was cooled in an ice bath and the solution was stirred with a magnetic stirring bar. A solution of sodium aluminate (73.2 g, 43% wt/wt in water) was added into the beaker. Then a solution of aluminum sulfate hydrate (59.3 g, 48% wt/wt in water) was added into the beaker. The resulting mixture was a clear solution with a pH value of 6.3. The molar ratio of lactate to aluminum of the solution was about 1.1:1. The neutralized aluminum salt solution obtained was used for SAP surface modification.

5.7 g of the neutralized aluminum salt solution, 2.0 g of ethylene carbonate, and 4.0 g of deionized water were mixed to give a clear solution. The resulting mixture was applied on the surface of 200 g of SAP preproduct A using a finely atomized spray from a Paasche VL sprayer while the SAP particles were fluidized in air and continuously mixed. The coated material was then heated in a convection oven at 185° C. for 40 minutes for surface crosslinking. The particulate superabsorbent polymer composition was then sieved with 20/100 mesh US standard sieves to remove particles greater than 850 μm and smaller than 150 μm.

Example 3

Same as Example 2 except the coated material was heated at 185° C. for 70 minutes.

Example 4

Into a polyethylene vessel equipped with an agitator and cooling coils was added, 2.0 kg of 50% NaOH and 3.32 kg of distilled water and cooled to 20° C. 0.8 kg of glacial acrylic acid was then added to the caustic solution and the solution again cooled to 20° C. 7.2 g of polyethylene glycol monoal-lylether acrylate, 7.2 g of ethoxylated trimethylol propane triacrylate SARTOMER® 454 product, and 1.6 kg of glacial acrylic acid were added to the first solution, followed by cooling to 4-6° C. Nitrogen was bubbled through the monomer solution for about 5 minutes. The monomer solution was then discharged into a rectangular tray. 80 g of 1% by weight of $H_2O_2$ aqueous solution, 120 g of 2 wt % aqueous sodium persulfate solution, and 72 g of 0.5 wt % aqueous sodium erythorbate solution was added into the monomer solution to initiate polymerization reaction. The agitator was stopped and the initiated monomer was allowed to polymerize for 20 minutes. The resulting hydrogel was chopped and extruded with a Hobart 4M6 commercial extruder, followed by drying in a Procter & Schwartz Model 062 forced air oven at 175° C. for 12 minutes with up flow and 6 minutes with down flow air on a 20 inch ×40 inch perforated metal tray to a final product moisture level of less than 5 wt %. The dried material was coarse-ground in a Prodeva Model 315-S crusher, milled in an MPI 666-F three-stage roller mill and sieved with a Minox MTS 600DS3V to remove particles greater than 850 μm and smaller than 150 μm. The SAP preproduct obtained was then subjected to the surface modification.

The same neutralized aluminum salt solution as described in Example 2 was used for SAP surface modification. 5.7 g of the neutralized aluminum salt solution, 2.0 g of ethylene carbonate, and 4.0 g of deionized water were mixed to give a clear solution. The resulting mixture was applied on the surface of 200 g of SAP preproduct obtained herein using a finely atomized spray from a Paasche VL sprayer while the SAP particles were fluidized in air and continuously mixed. The coated material was then heated in a convection oven at 185° C. for 55 minutes for surface crosslinking. The particulate superabsorbent polymer composition was then sieved with 20/100 mesh US standard sieves to remove particles greater than 850 μm and smaller than 150 μm.

Example 5

To a 100-ml beaker were added 1.60 g of glycolic acid (commercially available from Sigma-Aldrich) and 12.95 g of water. The beaker was cooled in an ice bath and the solution was stirred with a magnetic stirring bar. A solution of sodium aluminate (10.18 g, 20% wt/wt in water) was added into the beaker. Then a solution of aluminum sulfate hydrate (4.84 g, 40% wt/wt in water) was added into the beaker. The resulting mixture was a clear solution with a pH value of 6.6. The molar ratio of glycolate to aluminum of the solution was about 0.7:1. The neutralized aluminum salt solution obtained was used for SAP surface modification.

9.86 g of the neutralized aluminum salt solution obtained herein and 2.0 g of ethylene carbonate were mixed to give a clear solution. The resulting mixture was applied on the surface of 200 g of SAP preproduct A using a finely atomized spray from a Paasche VL sprayer while the SAP particles were fluidized in air and continuously mixed. The coated material was then heated in a convection oven at 185° C. for 55 minutes for surface crosslinking The particulate superabsorbent polymer composition was then sieved with 20/100 mesh US standard sieves to remove particles greater than 850 μm and smaller than 150 μm.

Example 6

To a 100-ml beaker were added 1.92 g of glycolic acid (commercially available from Sigma-Aldrich) and 13.01 g of water. The beaker was cooled in an ice bath and the solution was stirred with a magnetic stirring bar. A solution of sodium aluminate (10.37 g, 20% wt/wt in water) was added into the beaker. Then a solution of aluminum sulfate hydrate (4.49 g, 40% wt/wt in water) was added into the beaker. The resulting mixture was a clear solution with a pH value of 6.0. The molar ratio of glycolate to aluminum of the solution was about 0.81:1. The neutralized aluminum salt solution obtained was used for SAP surface modification.

9.93 g of the neutralized aluminum salt solution obtained herein and 2.0 g of ethylene carbonate, were mixed to give a clear solution. The resulting mixture was applied on the surface of 200 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The particulate superabsorbent polymer composition was then sieved with 20/100 mesh US standard sieves to remove particles greater than 850 μm and smaller than 150 μm.

Example 7

To a 100-ml beaker were added 2.26 g of glycolic acid (commercially available from Sigma-Aldrich) and 13.07 g of water. The beaker was cooled in an ice bath and the solution was stirred with a magnetic stirring bar. A solution of sodium aluminate (10.58 g, 20% wt/wt in water) was added into the beaker. Then a solution of aluminum sulfate hydrate (4.11 g, 40% wt/wt in water) was added into the beaker. The resulting mixture was a clear solution with a pH value of 6.2. The molar ratio of glycolate to aluminum of the solution was about 0.95:1. The neutralized aluminum salt solution obtained was used for SAP surface modification.

10.01 g of the neutralized aluminum salt solution obtained herein and 2.0 g of ethylene carbonate were mixed to give a clear solution. The resulting mixture was applied on the surface of 200 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The particulate superabsorbent polymer composition was then sieved with 20/100 mesh US standard sieves to remove particles greater than 850 μm and smaller than 150 μm.

Example 8

The same neutralized aluminum salt solution as described in Example 2 was used for SAP surface modification. 5.7 g of the neutralized aluminum salt solution, 0.4 g of ethylene glycole, and 4.0 g of deionized water were mixed to give a clear solution. The resulting mixture was applied on the surface of 200 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The particulate superabsorbent polymer composition was then sieved with 20/100 mesh US standard sieves to remove particles greater than 850 μm and smaller than 150 μm.

Example 9

The same neutralized aluminum salt solution as described in Example 2 was used for SAP surface modification. 5.7 g of the neutralized aluminum salt solution, 0.4 g of glycerol, and 4.0 g of deionized water were mixed to give a clear solution. The resulting mixture was applied on the surface of 200 g of SAP Preproduct A using a finely atomized spray from a Paasche VL sprayer while the particulate superabsorbent polymer were fluidized in air and continuously mixed. The coated material was then heated in a convection oven at 185° C. for 55 minutes for surface crosslinking. The particulate superabsorbent polymer composition was then sieved with 20/100 mesh US standard sieves to remove particles greater than 850 μm and smaller than 150 μm.

Example 10

The same neutralized aluminum salt solution as described in Example 2 was used for SAP surface modification. 5.7 g of the neutralized aluminum salt solution, 2.0 g of ethylene carbonate, and 2.0 g of deionized water were mixed to give a clear solution. The resulting mixture was applied on the surface of 200 g of SAP Preproduct A using a finely atomized spray from a Paasche VL sprayer while the SAP particles were fluidized in air and continuously mixed. Then a slurry containing 1.0 g of Kaolin (commercially available from Thiele Kaolin Company, Sanderville, Ga. 31082 USA) and 2.75 g of water was sprayed on SAP particles. The coated material was heated in a convection oven at 185° C. for 55 minutes for surface crosslinking. The particulate superabsorbent polymer composition was then sieved with 20/100 mesh US standard sieves to remove particles greater than 850 μm and smaller than 150 μm.

Example 11

A solution containing 2.0 g of ethylene carbonate, and 6.0 g of deionized water was applied on the surface of 200 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The particulate superabsorbent polymer composition was subjected with additional surface treatment with the same neutralized aluminum salt solution as described in Example 2. 5.7 g of the neutralized aluminum salt solution, 0.2 g of polyethylene glycol (molecular weight 8000), and 4.0 g of deionized water were mixed to give a clear solution. The resulting mixture was applied on the surface crosslinked particulate material obtained herein using a finely atomized spray from a Paasche VL sprayer while the SAP particles were fluidized in air and continuously mixed. The coated material was relaxed at room temperature for at least 1 hour before testing.

Example 12

The same neutralized aluminum salt solution as described in Example 2 was used for SAP surface modification. 5.7 g of the neutralized aluminum salt solution, 0.2 g of polyethylene glycol (molecular weight 8000), and 4.0 g of deionized water were mixed to give a clear solution. The resulting mixture was applied on the particulate superabsorbent polymer composition obtained in Example 2 using a finely atomized spray from a Paasche VL sprayer while the SAP particles were fluidized in air and continuously mixed. The coated material was relaxed at room temperature for at least 1 hour before testing.

Example 13

The same neutralized aluminum salt solution as described in Example 2 was used for SAP surface modification. 5.7 g of the neutralized aluminum salt solution, 0.2 g of polyethylene glycol (molecular weight 8000), and 4.0 g of deionized water were mixed to give a clear solution. The resulting mixture was applied on the particulate superabsorbent polymer composition obtained in Example 4 using a finely atomized spray from a Paasche VL sprayer while the SAP particles were fluidized in air and continuously mixed. The coated material was relaxed at room temperature for at least 1 hour before testing.

Example 14

Into a polyethylene vessel equipped with an agitator and cooling coils was added, 2.0 kg of 50% NaOH and 3.32 kg of distilled water and cooled to 20° C. 0.8 kg of glacial acrylic acid was then added to the caustic solution and the solution again cooled to 20° C. 8.2 g of polyethylene glycol monoallylether acrylate, 8.2 g of polyethylene glycol 300 diacrylate, and 1.6 kg of glacial acrylic acid were added to the first solution, followed by cooling to 4-6° C. Nitrogen was bubbled through the monomer solution for about 5 minutes.

The monomer solution was then discharged into a rectangular tray. 80 g of 1% by weight of $H_2O_2$ aqueous solution, 120 g of 2 wt % aqueous sodium persulfate solution, and 72 g of 0.5 wt % aqueous sodium erythorbate solution was added into the monomer solution to initiate polymerization reaction. The agitator was stopped and the initiated monomer was allowed to polymerize for 20 minutes. The resulting hydrogel was chopped and extruded with a Hobart 4M6 commercial extruder, followed by drying in a Procter & Schwartz Model 062 forced air oven at 175° C. for 12 minutes with up flow and 6 minutes with down flow air on a 20 inch×40 inch perforated metal tray to a final product moisture level of less than 5 wt %. The dried material was coarse-ground in a Prodeva Model 315-S crusher, milled in an MPI 666-F three-stage roller mill and sieved with a Minox MTS 600DS3V to remove particles greater than 850 μm and smaller than 150 μm. The preproduct obtained was then subjected to the surface modification.

The same neutralized aluminum salt solution as described in Example 2 was used for SAP surface modification. 5.7 g of the neutralized aluminum salt solution, 2.0 g of ethylene carbonate, and 4.0 g of deionized water were mixed to give a clear solution. The resulting mixture was applied on the surface of 200 g of SAP preproduct obtained herein using a finely atomized spray from a Paasche VL sprayer while the SAP particles were fluidized in air and continuously mixed. The coated material was then heated in a convection oven at 185° C. for 70 minutes for surface crosslinking The particulate superabsorbent polymer composition was then sieved with 20/100 mesh US standard sieves to remove particles greater than 850 μm and smaller than 150 μm.

The results of the above comparative examples and examples are summarized in the following table.

TABLE 1

| Particulate superabsorbent polymer composition | pH of aluminum sat solution | CRC (g/g) | 0.9 psi AUL (g/g) | GBP (Darcy) | 0.3 psi GBP (Darcy) |
|---|---|---|---|---|---|
| Comparative Example 1 | 2.8 | 34 | 17.4 | 23 | 0.6 |
| Comparative Example 2 | 3.7 | 32.6 | 22.9 | 7 | 1.9 |
| Comparative Example 3 | 1 | 32 | 19.9 | 13 | 2 |
| Comparative Example 4 | 2.8 | 32.6 | 20.9 | 12 | 1.6 |
| Comparative Example 5 | 14 | 32 | 19.7 | 4 | 0.5 |
| Comparative Example 6 | 6.4 | 32.7 | 23.2 | 7 | 1.8 |
| Comparative Example 7 | 7 | 32.1 | 22.6 | 4 | n/a |
| Example 1 | 6.5 | 32 | 18.8 | 37 | 1.9 |
| Example 2 | 6.3 | 33.1 | 19.4 | 33 | n/a |
| Example 3 | 6.3 | 31.1 | 18.2 | 56 | n/a |
| Example 4 | 6.3 | 28 | 19.4 | 69 | n/a |
| Example 5 | 6.6 | 31.9 | 20.1 | 38 | 1.6 |
| Example 6 | 6.0 | 32.8 | 19.3 | 39 | 1.7 |
| Example 7 | 6.2 | 33.1 | 19.8 | 31 | 1.6 |
| Example 8 | 6.3 | 32.3 | 18.5 | 38 | 1.3 |
| Example 9 | 6.3 | 32.6 | 18.1 | 36 | 1.6 |
| Example 10 | 6.3 | 32.1 | 19.5 | 46 | 2.5 |
| Example 11 | 63 | 31 | 18.1 | 48 | 1.1 |
| Example 12 | 6.3 | 32.4 | 20 | 42 | 2 |
| Example 13 | 6.3 | 27.3 | 19.1 | 81 | 6.6 |
| Example 14 | 6.3 | 33.9 | 18.6 | 41 | n/a |

Table 2 summarizes the calculated GBP values according to the equations of $GBP = 8{,}000\, e^{-0.18x}$ and $GBP = 10{,}500\, e^{-0.18x}$, where $x = CRC$.

TABLE 2

| Particulate superabsorbent polymer composition | pH of aluminum sat solution | CRC (g/g) | GBP = $8000\, e^{-0.18x}$ (Darcy) | GBP = $10500\, e^{-0.18x}$ (Darcy) |
|---|---|---|---|---|
| Comparative Example 1 | 2.8 | 34 | 17.6 | 23.1 |
| Comparative Example 2 | 3.7 | 32.6 | 22.6 | 29.7 |
| Comparative Example 3 | 1 | 32 | 25.2 | 33.1 |
| Comparative Example 4 | 2.8 | 32.6 | 22.6 | 29.7 |
| Comparative Example 5 | 14 | 32 | 25.2 | 33.1 |
| Comparative Example 6 | 6.4 | 32.7 | 22.2 | 29.2 |
| Comparative Example 7 | 7 | 32.1 | 24.8 | 32.5 |
| Example 1 | 6.5 | 32 | 25.2 | 33.1 |
| Example 2 | 6.3 | 33.1 | 20.7 | 27.1 |
| Example 3 | 6.3 | 31.1 | 29.6 | 38.9 |
| Example 4 | 6.3 | 28 | 51.8 | 68.0 |
| Example 5 | 6.6 | 31.9 | 25.7 | 33.7 |
| Example 6 | 6.0 | 32.8 | 21.8 | 28.6 |
| Example 7 | 6.2 | 33.1 | 20.7 | 27.1 |
| Example 8 | 6.3 | 32.3 | 23.9 | 31.3 |
| Example 9 | 6.3 | 32.6 | 22.6 | 29.7 |
| Example 10 | 6.3 | 32.1 | 24.8 | 32.5 |
| Example 11 | 63 | 31 | 30.2 | 39.6 |
| Example 12 | 6.3 | 32.4 | 23.5 | 30.8 |
| Example 13 | 6.3 | 27.3 | 58.7 | 77.1 |
| Example 14 | 6.3 | 33.9 | 17.9 | 23.5 |

The examples described for the process according to the invention all show a very good overall performance, characterized by high GBP and high AUL. Since the multivalent metal salts in the present invention have a pH value similar to that of human skin, superabsorbent polymer compositions according to the invention are expected to minimize the risk of skin irritation. The aluminum salts commonly used in prior arts are either acidic (Comparative Examples 1-4) or basic (Comparative Example 5). Furthermore, the GBP values in Comparative Examples 2-5 are rather low. The neutralized aluminum tri-lactate or aluminum citrate does not result in the desired GBP improvement. However, the surface treatment with an aluminum salt according to the present invention leads to the desired combination of properties.

Notwithstanding that the numerical ranges and parameters setting forth the broad scope of the invention are approximations, the numerical values set forth in the specific examples are reported as precisely as possible. Other than in the operating examples, or where otherwise indicated, all numbers expressing quantities of ingredients, reaction conditions, and so forth used in the specification and claims are to be understood as being modified in all instances by the term "about." Any numerical value, however, inherently contain certain errors necessarily resulting from the standard deviation found in their respective testing measurements.

What is claimed:

1. A particulate superabsorbent polymer composition comprising a polymer comprising:
   a) from about 55 wt % to about 99.9 wt % of polymerizable unsaturated acid group containing monomers;
   b) from 0 wt % to 40 wt % of polymerized, ethylenically unsaturated monomers copolymerizable with a);
   c) from about 0.001 wt % to about 5.0 wt % based on the weight of a) of an internal crosslinking agent, wherein the components a), b) and c) are polymerized into a hydrogel which is granulated into particulate superabsorbent polymer having a surface;

d) from about 0.001 wt % to about 5.0 wt % based on the dry particulate superabsorbent composition weight of surface crosslinking agent applied to the surface of the particulate superabsorbent polymer; and
e) from 0.01 wt % to about 5 wt % based on the dry particulate superabsorbent composition weight of a neutralized multivalent metal salt applied to the surface of the particulate superabsorbent polymer, wherein said neutralized multivalent metal salt further comprises an organic acid or its salt, wherein the molar ratio of said organic acid to the multivalent metal is between about 0.75:1 to about 1.5:1, and wherein the neutralized multivalent metal is in the form of an aqueous solution having a pH value from about 5.5 to about 7
wherein the superabsorbent polymer composition has a degree of neutralization of from about 50 mol % to about 80 mol %; and the particulate superabsorbent polymer composition have a Gel Bed Permeability of from about 30 Darcy to about 100 Darcy as measured by the Free-Swell Gel Bed Permeability Test as set forth herein; a Centrifuge Retention Capacity of from about 25 g/g to about 50 g/g as measured by the Centrifuge Retention Capacity Test as set forth herein, and an absorbency under load at 0.9 psi from about 16 g/g to 24 g/g as measured by the Absorbency Under Load Test (AUL(0.9 psi)) as set forth herein.

2. The particulate superabsorbent polymer composition according to claim 1 wherein the Centrifuge Retention Capacity is from about 27 g/g to about 35 g/g.

3. The particulate superabsorbent polymer composition according to claim 1 wherein the Centrifuge Retention Capacity is from about 30 g/g to about 35 g/g.

4. The particulate superabsorbent polymer composition according to claim 1 wherein said neutralized multivalent metal salt has a pH value from about 6 to 7.

5. The particulate superabsorbent polymer composition according to claim 1 wherein said neutralized multivalent metal salt is a water-soluble aluminum salt.

6. The particulate superabsorbent polymer composition according to claim 1 wherein said organic acid is a hydroxyl mono-carboxylic acid.

7. The particulate superabsorbent polymer composition according to claim 1 wherein said organic acid is selected from lactic acid, glycolic acid, gluconic acid, or 3-hydroxypropionic acid.

8. A particulate superabsorbent polymer composition comprising a polymer comprising:
a) from about 55 wt % to about 99.9 wt % of polymerizable unsaturated acid group containing monomers;
b) from 0 wt % to 40 wt % of polymerized, ethylenically unsaturated monomers copolymerizable with a);
c) from about 0.001 wt % to about 5.0 wt % based on the weight of a) of an internal crosslinking agent, wherein the components a), b) and c) are polymerized into a hydrogel which is granulated into particulate superabsorbent polymer having a surface;
d) from about 0.001 wt % to about 5.0 wt % based on the dry particulate superabsorbent composition weight of surface crosslinking agent applied to the surface of the particulate superabsorbent polymer; and
e) from about 0.01 wt % to about 5 wt % based on the dry particulate superabsorbent composition weight of aluminum salt applied to the surface of the particulate superabsorbent polymer, wherein said aluminum salt further comprises a deprotonated hydroxyl mono-carboxylic acid or its salt, and wherein the aluminum salt is in the form of an aqueous solution having a pH value from about 5.5 to about 7
wherein said aluminum salt solution comprises aluminum cations and anions of a deprotonated hydroxyl monocarboxylic acid with a molar ratio of carboxylic anions to aluminum cations between about 0.75:1 to about 1.5:1, wherein the superabsorbent polymer composition has a degree of neutralization of from about 50 mol % to about 80 mol %; and the particulate superabsorbent polymer composition have a Gel Bed Permeability of from about 30 Darcy to about 100 Darcy as measured by the Free-Swell Gel Bed Permeability Test set forth herein; a Centrifuge Retention Capacity of from about 25 g/g to about 50 g/g as measured by the Centrifuge Retention Capacity Test set forth herein, and an absorbency under load at 0.9 psi from about 16 g/g to 24 g/g as measured by the Absorbency Under Load Test (AUL (0.9 psi)) set forth herein.

9. The particulate superabsorbent polymer composition according to claim 8 wherein the Centrifuge Retention Capacity is from about 27 g/g to about 35 g/g.

10. The particulate superabsorbent polymer composition according to claim 8 wherein the Centrifuge Retention Capacity is from about 30 g/g to about 35 g/g.

11. The particulate superabsorbent polymer composition according to claim 8 wherein said neutralized multivalent metal salt has a pH value from about 6 to 7.

12. A process for the production of a particulate superabsorbent polymer composition comprising the following steps:
a) providing a particulate superabsorbent polymer;
b) preparing a neutralized multivalent metal salt wherein said neutralized multivalent metal salt further comprises a deprotonated organic acid or its salt, wherein the molar ratio of said organic acid to multivalent metal is between about 0.75:1 to about 1.5:1, and wherein the neutralized multivalent metal is in the form of an aqueous solution having a pH value from about 5.5 to about 7;
c) applying the neutralized multivalent metal salt solution on the surface of the particulate superabsorbent polymer wherein
wherein the particulate superabsorbent polymer composition has a degree of neutralization of from about 50 mol % to about 80 mol %; and the particulate superabsorbent polymer composition has the characteristics of a Gel Bed Permeability of from about 30 Darcy to about 100 Darcy as measured by the Free-Swell Gel Bed Permeability Test set forth herein; a Centrifuge Retention Capacity from about 25 g/g to about 50 g/g as measured by the Centrifuge Retention Capacity Test set forth herein, and an absorbency under load at 0.9 psi from about 16 g/g to 24 g/g as measured by the Absorbency Under Load Test (AUL(0.9 psi)) set forth herein.

13. The process according to claim 12 wherein said neutralized multivalent metal salt is aluminum salt.

14. The process according to claim 12 wherein said deprotonated organic acid is a hydroxyl mono-carboxylic acid.

15. The process according to claim 12 wherein said deprotonated organic acid is selected from lactic acid, glycolic acid, gluconic acid, or 3-hydroxypropionic acid.

16. The process according to claim 12 wherein the amount of the neutralized multivalent metal salt is from 0.01 wt % to about 5 wt % based on the dry particulate superabsorbent composition.

17. The process according to claim 12 wherein said aqueous solution has a pH value from about 6 to 7.

18. A process for the production of a particulate superabsorbent polymer composition comprising the following steps:
   a) providing a particulate superabsorbent polymer;
   b) bringing the superabsorbent polymer into contact with an aqueous solution of comprising a multivalent cation and an anion of a deprotonated organic acid with a molar ratio of organic acid to multivalent cation between about 0.75:1 to about 1.5:1;
      wherein said aqueous solution has a pH value from about 5.5 to about 7; and said organic acid is a hydroxyl mono-carboxylic acid
      wherein the particulate superabsorbent polymer composition has a degree of neutralization of from about 50 mol % to about 80 mol %; and the particulate superabsorbent polymer composition has the characteristics of a Gel Bed Permeability of from about 30 Darcy to about 100 Darcy as measured by the Free-Swell Gel Bed Permeability Test set forth herein; a Centrifuge Retention Capacity from about 25 g/g to about 50 g/g as measured by the Centrifuge Retention Capacity Test set forth herein, and an absorbency under load at 0.9 psi from about 16 g/g to 24 g/g as measured by the Absorbency Under Load Test (AUL(0.9 psi)) set forth herein.

19. The process according to claim 18 wherein said multivalent cation is aluminum cation $Al^{3+}$.

20. The process according to claim 18 wherein said organic acid is selected from lactic acid, glycolic acid, gluconic acid, or 3-hydroxypropionic acid.

21. The process according to claim 18 wherein said aqueous solution has a pH value from about 6 to 7.

22. An absorbent article comprising the particulate superabsorbent polymer composition of claim 1.

23. The particulate superabsorbent polymer composition according to claim 1 further comprising from about 0.01 wt % to about 0.5 wt % based on the dry particulate superabsorbent polymer composition of a thermoplastic polymer that is selected from polyolefin, polyethylene, linear low density polyethylene, ethylene acrylic acid copolymer, styrene copolymers, ethylene alkyl methacrylate copolymer, polypropylene, maleated polypropylene, ethylene vinyl acetate copolymer, polyamide, polyester, blends thereof, or copolymers thereof to form a thermoplastic coated particulate superabsorbent polymer.

24. The particulate superabsorbent polymer composition according to claim 23 wherein the thermoplastic polymer comprises maleated polypropylene.

25. The particulate superabsorbent polymer composition according to claim 1 having a water content of up to about 10 wt % of the superabsorbent polymer composition.

26. The particulate superabsorbent polymer composition according to claim 8 further comprising from about 0.01 wt % to about 0.5 wt % based on the dry particulate superabsorbent polymer composition of a thermoplastic polymer that is selected from polyolefin, polyethylene, linear low density polyethylene, ethylene acrylic acid copolymer, styrene copolymers, ethylene alkyl methacrylate copolymer, polypropylene, maleated polypropylene, ethylene vinyl acetate copolymer, polyamide, polyester, blends thereof, or copolymers thereof to form a thermoplastic coated particulate superabsorbent polymer.

27. The particulate superabsorbent polymer composition according to claim 26 wherein the thermoplastic polymer comprises maleated polypropylene.

28. The particulate superabsorbent polymer composition according to claim 8 having a water content of up to about 10 wt % of the superabsorbent polymer composition.

\* \* \* \* \*